(12) United States Patent
Kester et al.

(10) Patent No.: US 10,948,404 B2
(45) Date of Patent: Mar. 16, 2021

(54) GAS IMAGING SYSTEM

(71) Applicant: Rebellion Photonics, Inc., Houston, TX (US)

(72) Inventors: Robert Timothy Kester, Friendswood, TX (US); Ohad Israel Balila, Friendswood, TX (US)

(73) Assignee: REBELLION PHOTONICS, INC., Houston, TX (US)

( * ) Notice: Subject to any disclaimer, the term of this patent is extended or adjusted under 35 U.S.C. 154(b) by 0 days.

(21) Appl. No.: 15/789,829

(22) Filed: Oct. 20, 2017

(65) Prior Publication Data

US 2018/0188163 A1     Jul. 5, 2018

Related U.S. Application Data

(60) Provisional application No. 62/427,109, filed on Nov. 28, 2016, provisional application No. 62/411,499, filed on Oct. 21, 2016.

(51) Int. Cl.
*G01N 21/35* (2014.01)
*G01N 21/3504* (2014.01)
(Continued)

(52) U.S. Cl.
CPC ........ *G01N 21/3504* (2013.01); *G01J 3/0232* (2013.01); *G01J 3/28* (2013.01);
(Continued)

(58) Field of Classification Search
CPC ................. G01N 21/3504; G01N 2021/1795
See application file for complete search history.

(56) References Cited

U.S. PATENT DOCUMENTS 3,841,763 A    10/1974  Lewis
3,849,005 A *  11/1974  Girard ................ G01N 21/3518
                                          356/438

(Continued)

FOREIGN PATENT DOCUMENTS

CA    2 365 866    9/2000
CA    2 787 303    7/2011
(Continued)

OTHER PUBLICATIONS

US 10,113,914 B2, 10/2018, Kester et al. (withdrawn)
(Continued)

*Primary Examiner* — Hugh Maupin
(74) *Attorney, Agent, or Firm* — Alston & Bird LLP

(57) ABSTRACT

A spectral imaging system configured to obtain spectral measurements in a plurality of spectral regions is described herein. The spectral imaging system comprises at least one optical detecting unit having a spectral response corresponding to a plurality of absorption peaks of a target chemical species. In an embodiment, the optical detecting unit may comprise an optical detector array, and one or more optical filters configured to selectively pass light in a spectral range, wherein a convolution of the responsivity of the optical detector array and the transmission spectrum of the one or more optical filters has a first peak in mid-wave infrared spectral region between 3-4 microns corresponding to a first absorption peak of methane and a second peak in a long-wave infrared spectral region between 6-8 microns corresponding to a second absorption peak of methane.

20 Claims, 6 Drawing Sheets

(51) Int. Cl.
  *G01J 3/36* (2006.01)
  *G01J 3/02* (2006.01)
  *G01N 33/00* (2006.01)
  *G01M 3/38* (2006.01)
  *G01J 3/28* (2006.01)
  *G01N 21/17* (2006.01)
  *G01J 3/12* (2006.01)

(52) U.S. Cl.
  CPC .................. *G01J 3/36* (2013.01); *G01M 3/38* (2013.01); *G01N 33/0047* (2013.01); *G01J 2003/1213* (2013.01); *G01N 2021/1795* (2013.01); *G01N 2021/3531* (2013.01); *G01N 2201/0221* (2013.01)

(56) References Cited

U.S. PATENT DOCUMENTS

| | | | |
|---|---|---|---|
| 4,134,683 A | 1/1979 | Goetz et al. | |
| 4,205,229 A * | 5/1980 | Frosch | G01J 3/1809 |
| | | | 250/338.1 |
| 4,390,785 A | 6/1983 | Faulhaber et al. | |
| 4,464,789 A | 8/1984 | Sternberg | |
| 4,933,555 A | 6/1990 | Smith | |
| 4,963,963 A | 10/1990 | Dorman | |
| 4,965,448 A | 10/1990 | Morse et al. | |
| 5,127,742 A | 7/1992 | Fraden | |
| 5,136,421 A | 8/1992 | Sagan | |
| 5,157,258 A | 10/1992 | Gunning, III et al. | |
| 5,354,987 A | 10/1994 | MacPherson | |
| 5,430,293 A | 7/1995 | Sato et al. | |
| 5,550,373 A | 8/1996 | Cole et al. | |
| 5,559,336 A | 9/1996 | Kasai et al. | |
| 5,604,346 A | 2/1997 | Hamrelius et al. | |
| 5,800,360 A * | 9/1998 | Kisner | G08B 13/19 |
| | | | 600/532 |
| 5,822,222 A | 10/1998 | Kaplinsky et al. | |
| 5,877,500 A | 3/1999 | Braig et al. | |
| 5,890,095 A | 3/1999 | Barbour et al. | |
| 5,920,066 A | 7/1999 | DiRenzo et al. | |
| 5,926,283 A | 7/1999 | Hopkins | |
| 5,973,844 A | 10/1999 | Burger | |
| 5,994,701 A | 11/1999 | Tsuchimoto et al. | |
| 6,023,061 A | 2/2000 | Bodkin | |
| 6,097,034 A | 8/2000 | Weckström | |
| 6,184,529 B1 | 2/2001 | Contini | |
| 6,268,883 B1 | 7/2001 | Zehnder et al. | |
| 6,456,261 B1 | 9/2002 | Zhang | |
| 6,465,785 B1 | 10/2002 | McManus | |
| 6,556,853 B1 | 4/2003 | Cabib et al. | |
| 6,680,778 B2 | 1/2004 | Hinnrichs et al. | |
| 6,695,886 B1 | 2/2004 | Brown et al. | |
| 6,700,527 B1 | 3/2004 | Martin et al. | |
| 7,109,488 B2 | 9/2006 | Milton | |
| 7,119,337 B1 | 10/2006 | Johnson et al. | |
| 7,242,478 B1 | 7/2007 | Dombrowski et al. | |
| 7,315,377 B2 | 1/2008 | Holland et al. | |
| 7,321,119 B2 | 1/2008 | King | |
| 7,364,597 B2 | 4/2008 | McFarland et al. | |
| 7,433,042 B1 | 10/2008 | Cavanaugh et al. | |
| 7,606,484 B1 | 10/2009 | Richards et al. | |
| 7,634,157 B1 | 12/2009 | Richards et al. | |
| 7,750,802 B1 | 7/2010 | Parish et al. | |
| 7,835,002 B2 | 11/2010 | Muhammed et al. | |
| 7,888,624 B1 | 2/2011 | Murguia et al. | |
| 8,027,041 B1 | 9/2011 | Mitchell et al. | |
| 8,153,980 B1 | 4/2012 | Brady et al. | |
| 8,159,568 B2 | 4/2012 | Ahdoot | |
| 8,212,213 B2 | 7/2012 | Myrick et al. | |
| 8,373,757 B1 | 2/2013 | Nguyen | |
| 8,629,930 B2 | 1/2014 | Brueckner et al. | |
| 8,653,461 B1 | 2/2014 | Benson et al. | |
| 8,654,328 B2 | 2/2014 | Tkaczyk et al. | |
| 8,686,364 B1 | 4/2014 | Little et al. | |
| 9,225,913 B2 | 12/2015 | Ekdahl | |
| 9,395,516 B2 | 7/2016 | Katsunuma et al. | |
| 9,404,804 B1 * | 8/2016 | Liu | G01J 5/0014 |
| 9,552,849 B2 | 2/2017 | Kester et al. | |
| 9,599,508 B2 | 3/2017 | Kester et al. | |
| 9,612,195 B1 | 4/2017 | Friedman | |
| 9,625,318 B2 | 4/2017 | Kester et al. | |
| 9,541,772 B2 | 5/2017 | Yujiri | |
| 9,644,562 B2 | 5/2017 | Fujita | |
| 9,756,263 B2 | 9/2017 | Kester et al. | |
| 9,823,231 B1 * | 11/2017 | Steele | F17D 5/02 |
| 10,084,975 B2 | 9/2018 | Kester et al. | |
| 10,254,166 B2 | 4/2019 | Kester et al. | |
| 10,267,686 B2 | 4/2019 | Kester et al. | |
| 10,375,327 B2 | 8/2019 | Kester | |
| 10,416,076 B2 * | 9/2019 | Sandsten | G01N 21/3518 |
| 10,444,070 B2 | 10/2019 | Kester et al. | |
| 10,458,905 B2 | 10/2019 | Kester et al. | |
| 10,605,725 B2 | 3/2020 | Mallery et al. | |
| 10,648,960 B2 | 5/2020 | Kester et al. | |
| 2001/0040216 A1 | 11/2001 | Knauth et al. | |
| 2002/0015151 A1 | 2/2002 | Garin | |
| 2002/0121370 A1 | 9/2002 | Kurkjian et al. | |
| 2002/0159101 A1 | 10/2002 | Alderson et al. | |
| 2003/0102435 A1 | 6/2003 | Myers et al. | |
| 2003/0134426 A1 | 7/2003 | Jiang et al. | |
| 2003/0133756 A1 | 10/2003 | Huniu | |
| 2004/0093167 A1 | 5/2004 | Braig et al. | |
| 2004/0111232 A1 | 5/2004 | Butler et al. | |
| 2004/0252300 A1 | 12/2004 | Slater | |
| 2005/0029453 A1 | 2/2005 | Allen et al. | |
| 2005/0057366 A1 | 3/2005 | Kadwell et al. | |
| 2005/0103989 A1 | 5/2005 | Watson et al. | |
| 2005/0156111 A1 | 7/2005 | Racca et al. | |
| 2006/0044562 A1 | 3/2006 | Hagene et al. | |
| 2006/0183241 A1 | 8/2006 | Lehmann et al. | |
| 2006/0203248 A1 | 9/2006 | Reichardt et al. | |
| 2006/0232675 A1 | 10/2006 | Chamberlain et al. | |
| 2006/0279532 A1 | 12/2006 | Anderson | |
| 2007/0018105 A1 | 1/2007 | Grimberg | |
| 2007/0075888 A1 | 4/2007 | Kelly et al. | |
| 2007/0108385 A1 | 5/2007 | Mantese et al. | |
| 2007/0170357 A1 | 7/2007 | Arseneau | |
| 2007/0170359 A1 | 7/2007 | Syllaios et al. | |
| 2007/0170363 A1 | 7/2007 | Schimert et al. | |
| 2007/0268121 A1 | 11/2007 | Vasefi et al. | |
| 2008/0170140 A1 | 7/2008 | Silver et al. | |
| 2008/0204744 A1 | 8/2008 | Mir et al. | |
| 2008/0231719 A1 | 9/2008 | Benson et al. | |
| 2008/0251724 A1 * | 10/2008 | Baliga | G01J 3/02 |
| | | | 250/338.5 |
| 2009/0015824 A1 | 1/2009 | Shubinslw et al. | |
| 2009/0252650 A1 | 10/2009 | Lakshmanan | |
| 2010/0013979 A1 | 1/2010 | Golub et al. | |
| 2010/0162206 A1 | 6/2010 | Roth et al. | |
| 2010/0171866 A1 | 7/2010 | Brady et al. | |
| 2010/0211333 A1 | 8/2010 | Pruet et al. | |
| 2010/0309467 A1 | 12/2010 | Fox et al. | |
| 2011/0176577 A1 | 7/2011 | Bandara et al. | |
| 2011/0185048 A1 | 7/2011 | Yew et al. | |
| 2011/0261321 A1 | 10/2011 | Ramella-Roman et al. | |
| 2011/0271738 A1 | 11/2011 | McGill et al. | |
| 2011/0285995 A1 | 11/2011 | Tkaczyk et al. | |
| 2012/0154792 A1 | 6/2012 | Treado et al. | |
| 2012/0273680 A1 | 11/2012 | Furry | |
| 2012/0314080 A1 | 12/2012 | Lee et al. | |
| 2013/0181836 A1 | 7/2013 | Cardoso et al. | |
| 2013/0206990 A1 | 8/2013 | Hsu et al. | |
| 2013/0228887 A1 | 9/2013 | Wehner et al. | |
| 2013/0235256 A1 | 9/2013 | Kodama | |
| 2013/0250124 A1 * | 9/2013 | Furry | G01N 33/0036 |
| | | | 348/164 |
| 2013/0286213 A1 | 10/2013 | Cetin et al. | |
| 2013/0307991 A1 | 11/2013 | Olsen et al. | |
| 2013/0321806 A1 | 12/2013 | Kester et al. | |
| 2013/0341509 A1 | 12/2013 | Nelson et al. | |
| 2013/0342680 A1 * | 12/2013 | Zeng | H04N 5/332 |
| | | | 348/135 |
| 2014/0002639 A1 | 1/2014 | Cheben et al. | |
| 2014/0139643 A1 | 5/2014 | Högasten et al. | |

(56) References Cited

U.S. PATENT DOCUMENTS

| | | | |
|---|---|---|---|
| 2014/0320843 A1 | 10/2014 | Streuber et al. | |
| 2015/0069239 A1 | 3/2015 | Kester et al. | |
| 2015/0136981 A1 | 5/2015 | Kester et al. | |
| 2015/0136982 A1 | 5/2015 | Kester et al. | |
| 2015/0138534 A1 | 5/2015 | Tidhar | |
| 2015/0144770 A1 | 5/2015 | Choi | |
| 2015/0226613 A1 | 8/2015 | Bauer et al. | |
| 2015/0288894 A1 | 10/2015 | Geelen et al. | |
| 2015/0292948 A1 | 10/2015 | Goldring et al. | |
| 2015/0316473 A1 | 11/2015 | Kester et al. | |
| 2016/0037089 A1 | 2/2016 | Silny et al. | |
| 2016/0041095 A1 | 2/2016 | Rothberg et al. | |
| 2016/0097713 A1 | 4/2016 | Kester et al. | |
| 2016/0097714 A1 | 4/2016 | Zeng et al. | |
| 2016/0238449 A1 | 8/2016 | Goldring et al. | |
| 2016/0238454 A1 | 8/2016 | Pillans | |
| 2016/0245698 A1 | 8/2016 | Pau et al. | |
| 2016/0249228 A1 | 8/2016 | Zhao | |
| 2016/0313181 A1 | 10/2016 | Golub et al. | |
| 2016/0349228 A1 | 12/2016 | Kester et al. | |
| 2016/0356702 A1 | 12/2016 | Hinnrichs | |
| 2016/0379059 A1 | 12/2016 | Gottschlich | |
| 2016/0380014 A1 | 12/2016 | Ganapathi et al. | |
| 2017/0026588 A1 | 1/2017 | Kester et al. | |
| 2017/0059807 A1 | 3/2017 | Feng | |
| 2017/0089761 A1* | 3/2017 | McQuilkin | G01J 3/2803 |
| 2017/0138846 A1* | 5/2017 | Alizadeh | G01N 21/274 |
| 2017/0138918 A1 | 5/2017 | Bardoni | |
| 2017/0205290 A1 | 7/2017 | Kester et al. | |
| 2017/0234761 A1 | 8/2017 | Augusto | |
| 2017/0248517 A1* | 8/2017 | Scherer | G01N 21/3504 |
| 2017/0347037 A1 | 11/2017 | Hail et al. | |
| 2017/0350758 A1 | 12/2017 | Kester et al. | |
| 2017/0356802 A1 | 12/2017 | Kester et al. | |
| 2018/0039885 A1 | 2/2018 | Albrecht et al. | |
| 2018/0077363 A1 | 3/2018 | Kester et al. | |
| 2018/0188163 A1 | 7/2018 | Kester et al. | |
| 2018/0191967 A1 | 7/2018 | Kester | |
| 2019/0003984 A1 | 1/2019 | Kester et al. | |
| 2019/0137388 A1 | 5/2019 | Mallery et al. | |
| 2019/0273875 A1 | 9/2019 | Kester et al. | |
| 2019/0373185 A1 | 12/2019 | Kester | |
| 2020/0072671 A1 | 3/2020 | Kester et al. | |
| 2020/0088586 A1 | 3/2020 | Kester et al. | |
| 2020/0124470 A1 | 4/2020 | Kester et al. | |
| 2020/0124525 A1 | 4/2020 | Kester et al. | |
| 2020/0128196 A1 | 4/2020 | Kester | |
| 2020/0132596 A1 | 4/2020 | Mallery et al. | |

FOREIGN PATENT DOCUMENTS

| | | |
|---|---|---|
| CA | 2870419 A1 | 5/2015 |
| EP | 0 837 600 | 4/1998 |
| EP | 2 871 452 | 5/2015 |
| EP | 2870419 A1 | 5/2015 |
| EP | 2942615 A1 | 11/2015 |
| EP | 2 955 496 | 12/2015 |
| EP | 3 040 706 | 7/2016 |
| GB | 1014769 | 12/1965 |
| GB | 2518224 | 3/2015 |
| JP | 2013-128185 | 6/2013 |
| WO | WO 2004/097389 | 11/2004 |
| WO | WO 2007/008825 | 1/2007 |
| WO | WO 2008/109183 | 9/2008 |
| WO | WO 2009/094782 | 8/2009 |
| WO | WO 2010/053979 | 5/2010 |
| WO | WO 2012/078417 | 6/2012 |
| WO | WO 2012/082366 | 6/2012 |
| WO | WO 2013/173541 | 11/2013 |
| WO | 2014/008137 A1 | 1/2014 |
| WO | WO 2015/108236 | 7/2015 |
| WO | WO 2016/196224 | 12/2016 |
| WO | WO 2017/201194 | 11/2017 |
| WO | WO 2018/075957 | 4/2018 |
| WO | WO 2018/075964 | 4/2018 |
| WO | WO 2018/156795 | 8/2018 |
| WO | WO 2019/094639 | 5/2019 |

OTHER PUBLICATIONS

Adams, et al., "Advances in Detectors: HOT IR sensors improve IR camera size, weight, and power", Laser Focus World, vol. 50, Issue 01, Jan. 17, 2014, 6 pages. Also available at http://www.ircameras.com/articles/advances-detectors-hot-ir-sensors-improve-ir-camera-size-weight-power/.

Allen et al., "Measurements of Methane Emissions at Natural Gas Production Sites in the United States", PNAS, Oct. 29, 2013, vol. 110, No. 44, pp. 7.

Alvarez et al., "Greater Focus Needed on Methane Leakage from Natural Gas Infrastructure", PNAS, Apr. 24, 2012, vol. 109, No. 17, pp. 12.

Bedard et al., "Image Mapping Spectrometry: Calibration and Characterization", Optical Engineering, Nov. 2012, vol. 51, No. 11, pp. 111711-1-111711-13.

Ben-David et al., "Probability Theory for 3-Layer Remote Sensing Radiative Transfer Model: Univariate Case," Optics Express, Apr. 2012, vol. 20, No. 9, pp. 10004-10033.

Ben-David et al., "Probability Theory for 3-Layer Remote Sensing Radiative Transfer Model: Errata," Optics Express, May 20, 2013, vol. 21, No. 10, pp. 11852.

Brady et al., "Multiscale Lens Design", Optics Express, Jun. 22, 2009, vol. 17, No. 13, pp. 10659-10674.

Brochure provided by Lofty Designs to Rebellion Photonics on Oct. 31, 2012 as noted from the email. Subsequent to that date brochure was used in connection with potential customers.

Caulton et al., "Toward a Better Understanding and Quantification of Methane Emissions from Shale Gas Development", PNAS, Apr. 29, 2014, vol. 111, No. 17, pp. 7.

Chen et al., "Quantitative Sectioning and Noise Analysis for Structured Illumination Microscopy: Erratum", Optics Express, Oct. 19, 2015, vol. 23, No. 21, pp. 27633-27534.

Chidley et al., "Flow-Induced Birefringence: The Hidden PSF Killer in High Performance Injection-Molded Plastic Optics", Endoscopic Microscopy, Proceedings of SPIE vol. 6082, 2006, pp. 11.

Chu et al., "The NIST Quantitative Infrared Database", Journal of Research of the National Institute of Standards and Technology, Jan.-Feb. 1999, vol. 104, No. 1, pp. 59-81.

Cossel et al., "Analysis of Trace Impurities in Semiconductor Gas Via Cavity-Enhanced Direct Frequency Comb Spectroscopy", Applied Physics B, Sep. 2010, vol. 100, No. 4, pp. 917-924.

DiPietro et al., "Hyperspectral Matched Filter with False-Alarm Mitigation", Optical Engineering, Jan. 2012, vol. 51, No. 1, pp. 016202-1-015202-7.

"Directed Inspection and Maintenance at Gas Processing Plants and Booster Stations," United States Environmental Protection Agency Air and Radiation (6202J), EPA430-B-03-018, Oct. 2003 available at https://www3.epa.gov/gasstar/documents/II_dimgasproc.pdf.

Eriksson et al., "Radiative Cooling Computed for Model Atmospheres", Applied Optics, Dec. 1, 1982, vol. 21, No. 23, pp. 4381-4388.

Flanigan, "Detection of Organic Vapors with Active and Passive Sensors: A Comparison," Applied Optics, 1986, vol. 25, No. 23, pp. 4253-4260.

Gålfalk et al., "Making Methane Visible", Nature Climate Change, Apr. 2016, vol. 6, pp. 426-430.

Gålfalk et al., "Making Methane Visible", Supplementary Information, Nature Climate Change, 2015, pp. 1-14.

Gallagher et al., "Error Analysis for Estimation of Trace Vapor Concentration Pathlength in Stack Plumes", Applied Spectroscopy, 2003, vol. 57, No. 6, pp. 614-621.

Gallagher et al., "Estimation of Trace Vapor Concentration-Pathlength in Plumes for Remote Sensing Applications from Hyperspectral Images", Analytica Chimica Acta, 2003, vol. 490, pp. 139-152.

(56) References Cited

OTHER PUBLICATIONS

Gao et al., "Compact Image Slicing Spectrometer (ISS) for Hyperspectral Fluorescence Microscopy", Optics Express, Jul. 20, 2009, vol. 17, No. 15, pp. 12293-12308.
Gao et al., "Depth-Resolved Image Mapping Spectrometer (IMS) with Structured Illumination", Optics Express, Aug. 29, 2011, vol. 19, No. 18, pp. 17439-17452.
Gao et al., "Optical Design of a Snapshot High-Sampling Image Mapping Spectrometer (IMS) for Hyperspectral Microscopy", Three-Dimensional and Multidimensional Microscopy: Image Acquisition and Processing XVII, Proceedings of SPIE vol. 7570, 2010, pp. 1-7.
Gao et al., "Quantitative Comparison Between Full-Spectrum and Filter-Based Imaging in Hyperspectral Fluorescence Microscopy", Journal of Microscopy, 2012, vol. 245, No. 2, pp. 113-123.
Gao et al "Snapshot Image Mapping Spectrometer (IMS) with High Sampling Density for Hyperspectral Microscopy", Optics Express, Jul. 5, 2010, vol. 18, No. 4, pp. 14330-14344.
Gerhart et al., "Detection and Tracking of Gas Plumes in LWIR Hyperspectral Video Sequence Data," Algorithms and Technologies for Multispectral, Hyperspectral, and Ultraspectral Imagery XIX, 2013, SPIE Proceedings vol. 8743, pp. 1-14.
Gittins, Christopher M., "Detection and Characterization of Chemical Vapor Fugitive Emissions by Nonlinear Optimal Estimation: Theory and Simulation", Applied Optics, Aug. 10, 2009, vol. 48, No. 23, pp. 4545-4561.
Goldberg et al., "Dual Band MWIR/LWIR Focal Plane Array Test Results," Army Research Lab, Adelphi, MD, Aug. 1999, pp. 18.
Golowich et al., "Performance Limier of LWIR Gaseous Plume Quantification", Algorithms and Technologies for Multispectral, Hyperspectral, and Ultraspectral Imagery XVII, 2011, Proceedings of SPIE vol. 8048, pp. 1-12.
Griffin et al., "The Herschel—SPIRE 1-15 Instrument and its In-Flight Performance," Astronomy and Astrophysics, Jul. 1, 2010, vol. 518, pp. 7.
Gross et al., "Remote Identification and Quantification of Industrial Smokestack Effluents via Imaging Fourier-Transform Spectroscopy", Environmental Science & Technology, 2010, vol. 44, No. 24, pp. 9390-9397.
Gupta et al., "Miniature Snapshot Multispectral Imager," Optical Engineering, 2011, vol. 50, pp. 033203-1-033203-9.
Hadlington, Simon, "New Camera Makes Methane Visible", Chemistry World, http://web.archive.org/web/20160305234907/http://www.rsc.org/chemistryworld/2015/12/methane-camera-infrared-greenhouse-gas, Dec. 14, 2015, pp. 2.
Hagen et al., "Analysis of Computed Tomographic Imaging Spectrometers. I. Spatial and Spectral Resolution", Applied Optics, Oct. 1, 2008, vol. 47, No. 28, pp. F85-F95.
Hagen et al., "Coded Aperture DUV Spectrometer for Standoff Raman Spectroscopy", Next-Generation Spectroscopic Technologies II, Proceedings of SPIE vol. 7319, 2009, pp. 1-10.
Hagen et al., "Compound Prism Design Principles, I", Applied Optics, Sep. 1, 2011, vol. 50, No. 25, pp, 4998-5011.
Hagen et al., "Compound Prism Design Principles, II: Triplet and Janssen Prisms", Applied Optics, Sep. 1, 2011, vol. 50, No. 25, pp, 5012-5022.
Hagen et al., "Compound Prism Design Principles, III: Linear-in-Wavenumber and Optical Coherence Tomography Prisms", Applied Optics, Sep. 1, 2011, vol. 50, No. 25, pp. 5023-5030.
Hagen et al.,"Fourier Methods of Improving Reconstruction Speed for CTIS Imaging Spectrometers", Imaging Spectrometry XII, Proceedings of SPIE vol. 6661, 2007, pp. 11.
Hagen et al., "Foveated Endoscopic Lens", Journal of Biomedical Optics, Feb. 2012, vol. 17, No. 2, pp. 021104-1-021104-6.
Hagen et al., "Gaussian Profile Estimation in One Dimension", Applied Optics, Aug. 1, 2007, vol. 46, No. 22, pp. 5374-5383.
Hagen et al., "Gaussian Profile Estimation in Two Dimensions", Applied Optics, Dec. 20, 2008, vol. 47, No. 36, pp. 6842-6851.
Hagen et al., "Quantitative Sectioning and Noise Analysis for Structured Illumination Microscopy", Optics Express, Jan. 2, 2012, vol. 20, No. 1, pp. 403-413.
Hagen et al., "Quantitative Sectioning and Noise Analysis for Structured Illumination Microscopy: Errata", Optics Express, Feb. 27, 2012, vol. 20, No. 5, pp. 5343.
Hagen et al., "Real-Time Quantitative Hydrocarbon Gas Imaging with the Gas Cloud Imager (GCI)", Proceedings of SPIE, vol. 8358, Chemical, Biological, Radiological, Nuclear, and Explosives (CBRNE) Sensing XIII, May 1, 2012, pp. 7.
Hagen et al., "Review of Snapshot Spectral Imaging Technologies", Optical Engineering, Sep. 2013, vol. 52, No. 9, pp. 090901-1-090901-23.
Hagen et al., "Snapshot Advantage: A Review of the Light Collection Improvement for Parallel High-Dimensional Measurement Systems," Optical Engineering, Jun. 13, 2012, vol. 51, No. 11, p. 111702-1-111702-7.
Hagen et al., "Snapshot Mueller Matrix Spectropolarimeter" Optics Letters, Aug. 1, 2007, vol. 32, No. 15, pp. 2100-2102.
Hagen et al., "Spectrally-Resolved Imaging of Dynamic Turbid Media", Multimodal Biomedical Imaging VI, Proceedings of SPIE vol. 7892, 2011, pp. 1-7.
Hagen et al., "Video-Rate Spectral Imaging of Gas Leaks in the Longwave Infrared," Chemical, Biological, Radiological, Nuclear, and Explosives (CBRNE) Sensing XIV, May 29, 2013, SPIE Proceedings vol. 8710, pp. 7.
Harley et al., "Remote Quantification of Smokestack Effluent Mass Flow Rates Using Imaging Fourier Transform Spectrometry," Chemical, Biological, Radiological, Nuclear, and Explosives (CBRNE) Sensing XII, Apr. 25-29, 2011, SPIE Proceedings vol. 8018, pp. 1-13.
Hayden et al., "Determination of Trace-Gas Amounts in Plumes by the Use of Orthogonal Digital Filtering of Thermal-Emission Spectra", Applied Optics, Jun. 1, 1996, vol. 35, No. 16, pp. 2802-2809.
Hirsch et al., "Detection of Gaseous Plumes in IR Hyperspectral Images Using Hierarchical Clustering", Applied Optics, Sep. 1, 2007, vol. 46, No. 25, pp. 6368-6374.
Johnston et al., "A Real-Time FPGA Implementation of a Barrel Distortion Correction Algorithm", Projects, 2003, vol. 10, pp. 91-96.
Karion et al., "Methane Emissions Estimate from Airborne Measurements Over a Western United States Natural Gas Field", Geophysical Research Letters, 2013, vol. 40, pp. 4393-4397.
Keshava et al., "A Survey of Spectral Unmixing Algorithms", Lincoln Laboratory Journal, 2003, vol. 14, No. 1, pp. 55-78.
Kester et al., "A Real-Time Gas Cloud Imaging Camera for Fugitive Emission Detection and Monitoring", Imaging and Applied Optics Technical Digest, 2012, pp. 3.
Kester et al., "Development of Image Mappers for Hyperspectral Biomedical Imaging Applications", Applied Optics, Apr. 1, 2010, vol. 49, No. 10, pp. 1886-1899.
Kester et al., "High Numerical Aperture Microendoscope Objective for a Fiber Confocal Reflectance Microscope", Optics Express, Mar. 5, 2007, vol. 15. No. 5, pp. 2409-2420.
Kester et al., "Low Cost, High Performance, Self-Aligning Miniature Optical Systems", Applied Optics, Jun. 20, 2009, vol. 48, No. 18, pp. 3375-3384.
Kester et al., "Real-Time Snapshot Hyperspectral Imaging Endoscope", Journal of Biomedical Optics, May 2011, vol. 16, No. 5, pp. 056005-1-055005-12.
Kudenov et al., "Fourier Transform Channeled Spectropolarimetry in the MWIR", Optics Express, Oct. 1, 2007, vol. 15, No. 20, pp. 12792-12805.
Kudenov et al., "Snapshot Imaging Mueller Matrix Polarirneter Using Polarization Gratings", Optics Letters, Apr. 15, 2012, vol. 37, No. 8, pp. 1367-1369.
Landau et al., "Design and Evaluation of an Ultra-Slim Objective for in-vivo Deep Optical Biopsy", Optics Express, Mar. 1, 2010, vol. 18, No. 5, pp. 4758-4775.
Levi, Michael A., "Comment on 'Hydrocarbon Emissions Characterization in the Colorado Front Range: A Pilot Study' by Gabrielle Pétron et al.", Journal of Geophysical Research, 2012, vol. 117, No. D21203, pp. 1-5.
Levi, Michael A., "Reply to "Reply to 'Comment on 'Hydrocarbon Emissions Characterization in the Colorado Front Range—A Pilot

(56) References Cited

OTHER PUBLICATIONS

Study' by Michael A. Levi'" by Gabrielle Pétron et al.", Journal of Geophysical Research: Atmospheres, 2013, vol. 118, pp. 3044-3046.
Low et al., "Remote Sensing and Characterization of Stack Gases by Infrared Spectroscopy. An Approach by Using Multiple-Scan Interferometry", Environmental Science & Technology, Jan. 1967, vol. 1, No. 1, pp. 73-74.
Luo et al., "Fast Processing of Imaging Spectrometer Data Cube Based on FPGA Design", MIPPR 2007: Multispectral Image Processing, Proceedings of SPIE vol. 6787, pp. 7.
Manolakis et al., "Long-Wave Infrared Hyperspectral Remote Sensing of Chemical Clouds", IEEE Signal Processing Magazine, Jul. 2014, vol. 31, No. 4, pp. 120-141.
Mathews, "Design and Fabrication of a Low-Cost, Multispectral Imaging System," Applied Optics, 2008, pp. F71-F76, vol. 47.
Naranjo et al., "IR Gas Imaging in an Industrial Setting," Thermosense XXXII, Published in SPIE Proceedings vol. 7661, May 4, 2010, pp. 1-8.
Nguyen et al., "Snapshot 3D Optical Coherence Tomography System using Image Mapping Spectrometer", Biomedical Optics and 3D Imaging OSA, 2012, pp. 3.
Niu et al., "New Approach to Remote Gas-Phase Chemical Quantification: Selected-Band Algorithm", Optical Engineering, Feb. 2014, vol. 53, No. 2, pp. 021111-1-021111-10.
"Oil and Natural Gas Sector Leaks", U.S. EPA Office of Air Quality Planning and Standards (OAQPS), Review Panel, Apr. 2014, pp. 63.
Pétron et al., "Hydrocarbon Emissions Characterization in the Colorado Front Range: A Pilot Study", Journal of Geophysical Research, 2012, vol. 117, No. D04304, pp. 1-19,
Pétron et al., "Reply to Comment on 'Hydrocarbon Emissions Characterization in the Colorado Front—A Pilot Study' by Michael A. Levi", Journal of Geophysical Research: Atmospheres, 2013, vol. 118, pp. 236-242.
Pisano et al., "Thermal Illuminators for Far-Infrared and Submillimeter Astronomical Instruments," Applied Optics, Jun. 1, 2005, vol. 44, No. 16, pp. 3208-3217.
Polak et al., "Passive Fourier-Transform Infrared Spectroscopy of Chemical Plumes: An Algorithm for Quantitative Interpretation and Real-Time Background Removal", Applied Optics, Aug. 20, 1995, vol. 34, No. 24, pp. 5406-5412.
Rebellion Photonics, "Gas Cloud Imaging Camera: A Breakthrough in Leak Monitoring for the Rig & Refinery Safety Market", Presentation at SPIE Defense Security and Sensing, 28 pages, Apr. 29-May 3, 2013.
Sandsten et al., "Development of Infrared Spectroscopy Techniques for Environmental Monitoring", Doctoral Thesis, Aug. 2000, pp. 123.
Sandsten et al., "Real-Time Gas-Correlation Imaging Employing Thermal Background Radiation", Optics Express, Feb. 14, 2000, vol. 6, No. 4, pp. 92-103.
Sandsten et al., "Volume Flow Calculations on Gas Leaks Imaged with Infrared Gas-Correlation," Optics Express, 2012, vol. 20, No. 18, pp. 20318-20329.
Shogenji et al., "Multispectral Imaging Using Compact Compound Optics," Optics Express, Apr. 19, 2004, vol. 12, No. 8, pp. 1643-1655.
Telops, "Hyper-Cam", http://web.archive.org/web/20160608180941/ http://www.telops.com/en/hyperspectral-cameras/hyper-cam as archived Jun. 8, 2016 in 2 pages.
Telops, "Innovative Infrared Imaging", http://web.archive.org/web/20160603212729/http://www.telops.com/en/ as archived Jun. 3, 2016 in 2 pages.
Walter Jr., et al., "Detection of Atmospheric Pollutants: a Correlation Technique", Applied Optics, Jun. 1975, vol. 14, No. 6, pp. 1423-1428.
Wikipedia entry https://en.wikipedia.org/wiki/Mobile_computing last modified on Dec. 30, 2016; retrieved from the Internet on Feb. 2, 2017 in 6 pages.
Williams et al., "Dual-Band MWIR/LWIR Radiometer for Absolute Temperature Measurements," SPIE Thermosense Conference XXVIII—Manuscript 6205-23, Apr. 18, 2006, pp. 13.
Young et al., "An In-Scene Method for Atmospheric Compensation of Thermal Hyperspectral Data", Journal of Geophysical Research, 2002, vol. 107, No. D24, pp. 14-1-14-20.
Zheng et al., "A Static Multiplex Fabry-Perot Spectrometer", Sensors, Cameras, and Systems for Industrial/Scientific Applications X, Proceedings of SPIE-IS&T Electronic Imaging, SPIE vol. 7249, 2009, pp. 8.
Zheng et al., "Analytic-Domain Lens Design with Proximate Ray Tracing", Journal of the Optical Society of America A, Aug. 2010, vol. 27, No. 8, pp. 1791-1802.
Preliminary Amendment as filed in U.S. Appl. No. 14/538,827 dated Jan. 28, 2015 in 6 pages.
Official Communication received in U.S. Appl. No. 14/538,827 dated Jun. 30, 2015 in 8 pages.
Non-Final Office Action Response as filed in U.S. Appl. No. 14/538,827 dated Dec. 28, 2015 in 11 pages.
Notice of Allowance received in U.S. Appl. No. 14/538,827 dated Feb. 1, 2016 in 18 pages.
Corrected Notice of Allowance received in U.S. Appl. No. 14/538,827 dated Feb. 10, 2016 in 4 pages.
Corrected Notice of Allowance received in U.S. Appl. No. 14/538,827 dated Feb. 22, 2016 in 4 pages.
Request for Continued Examination and Response to Correct Application Papers as filed in U.S. Appl. No. 14/538,827 dated Apr. 29, 2016 in 14 pages.
Notice of Allowance received in U.S. Appl. No. 14/538,827 dated May 26, 2016 in 9 pages.
Notice of Allowance received in U.S. Appl. No. 14/538,827 dated Sep. 19, 2016 in 9 pages.
Amendment as filed in U.S. Appl. No. 14/538,827 dated Dec. 16, 2016 in 9 pages.
Official Communication received in U.S. Appl. No. 15/418,532 dated Jun. 23, 2017 in 7 pages.
Amendment as filed in U.S. Appl. No. 15/418,532 dated Nov. 22, 2017 in 8 pages.
Official Communication received in U.S. Appl. No. 15/418,532 dated Dec. 11, 2017 in 21 pages.
Notice of Allowance received in U.S. Appl. No. 15/418,532 dated Jun. 15, 2018 in 12 pages.
Corrected Notice of Allowance received in U.S. Appl. No. 15/418,532 dated Jul. 6, 2018 in 3 pages.
Amendment after Allowance as filed in U.S. Appl. No. 15/418,532 dated Sep. 14, 2018 in 6 pages.
Notice of Allowance received in U.S. Appl. No. 15/418,532 dated Dec. 5, 2018 in 11 pages.
Official Communication received in U.S. Appl. No. 14/543,692 dated Nov. 3, 2015 in 7 pages.
Interview Summary received in U.S. Appl. No. 14/543,692 dated Feb. 17, 2016 in 5 pages.
Response to Office Action as filed in U.S. Appl. No. 14/543,692 dated May 2, 2016 in 9 pages.
Official Communication received in U.S. Appl. No. 14/543,692 dated Jun. 1, 2016 in 18 pages.
Response to Final Action as filed in U.S. Appl. No. 14/543,692 dated Nov. 30, 2016 in 12 pages.
Notice of Allowance received in U.S. Appl. No. 14/543,692 dated Dec. 9, 2016 in 12 pages.
Amendment after Allowance as filed in U.S. Appl. No. 14/543,692 dated Mar. 3, 2017 in 6 pages.
Notice of Allowance received in U.S. Appl. No. 14/543,692 dated Mar. 17, 2017 in 4 pages.
Preliminary Amendment as filed in U.S. Appl. No. 15/471,398 dated Oct. 6, 2017 in 6 pages.
Notice of Allowance received in U.S. Appl. No. 14/571,398 dated Oct. 18, 2017 in 8 pages.
Notice of Allowance received in U.S. Appl. No. 14/571,398 dated Feb. 7, 2018 in 20 pages.
Notice of Allowance received in U.S. Appl. No. 14/571,398 dated Jul. 2, 2018 in 8 pages.

(56) References Cited

OTHER PUBLICATIONS

Notice of Allowance received in U.S. Appl. No. 14/571,398 dated Oct. 24, 2018 in 7 pages.
Official Communication received in U.S. Appl. No. 14/539,899 dated Mar. 26, 2015 in 6 pages.
Non-Final Office Action Response as filed in U.S. Appl. No. 14/539,899 dated Aug. 26, 2015 in 8 pages.
Official Communication received in U.S. Appl. No. 14/539,899 dated Dec. 11, 2015 in 9 pages.
Amendment as filed in U.S. Appl. No. 14/539,899 dated Jun. 9, 2016 in 6 pages.
Notice of Allowance received in U.S. Appl. No. 14/539,899 dated Jun. 21, 2016 in 17 pages.
Notice of Allowance received in U.S. Appl. No. 14/539,899 dated Oct. 31, 2016 in 10 pages.
Amendment as filed in U.S. Appl. No. 14/539,899 dated Jan. 27, 2017 in 5 pages.
Official Communication received in U.S. Appl. No. 15/462,352 dated Sep. 28, 2017 in 6 pages.
Amendment as filed in U.S. Appl. No. 15/462,352 dated Feb. 28, 2018 in 5 pages.
Notice of Allowance received in U.S. Appl. No. 15/462,352 dated Jul. 17, 2018 in 25 pages.
Notice to File Corrected Application Paper's received in U.S. Appl. No. 15/462,352 dated Aug. 8, 2018 in 3 pages.
Response to Notice to File Corrected Application Papers filed in U.S. Appl. No. 15/462,352 dated Oct. 8, 2018 in 3 pages.
Notice of Allowance received in U.S. Appl. No. 15/462,352 dated Oct. 31, 2018 in 9 pages.
Official Communication received in European Application No. 13732285.5 dated Jul. 26, 2018 in 6 pages.
Extended European Search Report received in European Application No. 14192862.2 dated Mar. 30, 2015 in 10 pages.
Official Communication received in European Application No. 14192862.2 dated Apr. 19, 2016 in 6 pages.
Official Communication received in European Application No. 14192862.2 dated May 2, 2018 in 3 pages.
International Search Report in PCT Application No. PCT/US2013/041278 dated Aug. 27, 2013 in 4 pages.
International Preliminary Report on Patentability in PCT Application No. PCT/US2013/041278 dated Nov. 27, 2014 in 10 pages.
Preliminary Amendment as filed in U.S. Appl. No. 14/700,791 dated Jul. 13, 2015 in 8 pages.
Notice of Allowance received in U.S. Appl. No. 14/700,791 dated Jun. 9, 2016 in 11 pages.
Notice of Allowance received in U.S. Appl. No. 14/700,791 dated Sep. 30, 2016 in 19 pages.
Notice of Allowance received in U.S. Appl. No. 14/700,791 dated Feb. 21, 2017 in 20 pages.
Comments on Allowance filed in U.S. Appl. No. 14/700,791 dated May 19, 2017 in 2 pages.
Notice of Allowance received in U.S. Appl. No. 14/700,791 dated Jul. 10, 2017 in 24 pages.
Preliminary Amendment as filed in U.S. Appl. No. 15/623,942 dated Dec. 7, 2017 in 6 pages.
Notice of Allowance received in U.S. Appl. No. 15/623,942 dated Jan. 24, 2018 in 22 pages.
Notice of Allowance received in U.S. Appl. No. 15/623,942 dated May 24, 2018 in 23 pages.
Comments on Allowance filed in U.S. Appl. No. 15/623,942 dated Aug. 23, 2018 in 2 pages.
Extended European Search Report received in European Application No. 15165877.0 dated Oct. 8, 2015 in 12 pages.
Official Communication received in European Application No. 15165877.0 dated Jan. 3, 2017 in 9 pages.
Preliminary Amendment as filed in U.S. Appl. No. 14/700,567 dated Jul. 10, 2015 in 6 pages.
Publication Request as filed in U.S. Appl. No. 14/700,567 dated Aug. 24, 2016 in 237 pages.
Official Communication received in U.S. Appl. No. 14/700,567 dated Jun. 14, 2017 in 29 pages.
Amendment as filed in U.S. Appl. No. 14/700,567 dated Dec. 13, 2017 in 12 pages.
Official Communication received in U.S. Appl. No. 14/700,567 dated Mar. 5, 2018 in 38 pages.
Amendment as filed in U.S. Appl. No. 14/700,567 dated Jul. 5, 2018 in 10 pages.
Office Action as filed in U.S. Appl. No. 14/700,557 dated Aug. 27, 2018 in 35 pages.
Extended European Search Report received in European Application No. EP 15165880.4 dated Nov. 24, 2015 in 8 pages.
Preliminary Amendment as filed in U.S. Appl. No. 14/792,477 dated Dec. 21, 2015 in 7 pages.
Official Communication received in U.S. Appl. No. 14/792,477 dated Jan. 27, 2017 in 10 pages.
Response to Restriction Requirement submitted in U.S. Appl. No. 14/792,477 dated May 8, 2017 in 6 pages.
Official Communication received in U.S. Appl. No. 14/792,477 dated Jul. 19, 2017 in 20 pages.
Amendment as filed in U.S. Appl. No. 14/792,477 dated Jan. 18, 2018 in 10 pages.
Notice of Allowance received in U.S. Appl. No. 14/792,477 dated Apr. 19, 2018 in 13 pages.
Notice of Allowance received in U.S. Appl. No. 14/792,477 dated Sep. 20, 2018 in 14 pages.
Preliminary Amendment as filed in U.S. Appl. No. 15/166,092 dated Aug. 15, 2016 in 7 pages.
Offcial Communication received in U.S. Appl. No. 15/166,092 dated May 15, 2018 in 30 pages.
International Search Report in PCT Application No. PCT/US2016/034455 dated Oct. 24, 2016 in 12 pages.
International Preliminary Report on Patentability in PCT Application No. PCT/US2016/034455 dated Dec. 5, 2017 in 8 pages.
Preliminary Amendment as filed in U.S. Appl. No. 15/789,811 dated Mar. 20, 2018 in 6 pages.
Offcial Communication received in U.S. Appl. No. 15/789,811 dated Jul. 27, 2018 in 22 pages.
Invitation to Pay Additional Fees in PCT Application No. PCT/US2017/057725 dated Dec. 14, 2017 in 3 pages.
International Search Report in PCT Application No. PCT/US2017/057725 dated Feb. 14, 2018 in 14 pages.
Invitation to Pay Additional Fees in PCT Application No. PCT/US2017/057712 dated Jan. 10, 2018 in 2 pages.
International Search Report in PCT Application No. PCT/US2017/057712 dated Mar. 6, 2018 in 12 pages.
Preliminary Amendment as filed in U.S. Appl. No. 15/902,336 dated Sep. 20, 2018 in 9 pages.
International Search Report in PCT Application No. PCT/US2018/019271 dated Jun. 27, 2018 in 15 pages.
Weldon et al., "H2S and CO2 gas sensing using DFB laser diodes emitting at 1.57 µm", Sensors and Actuators B: Chemical, Oct. 1995, vol. 29, Issues 1-3, pp. 101-107.
Notice of Allowance received in U.S. Appl. No. 15/462,352 dated Feb. 12, 2019 in 9 pages.
Amendment as filed in U.S. Appl. No. 15/462,352 dated Apr. 30, 2019 in 5 pages.
Official Communication received in Canadian Application No. 2,873,989 dated Mar. 21, 2019 in 6 pages.
Notice of Allowance received in U.S. Appl. No. 14/792,477 dated Jan. 30, 2019 in 11 pages.
Amendment as filed in U.S. Appl. No. 15/166,092 dated Nov. 15, 2018 in 11 pages.
Extended European Search Report received in European Application No. EP 16804077.2 dated Jan. 8, 2019 in 8 pages.
Interview Summary received in U.S. Appl. No. 15/789,811 dated Nov. 20, 2018 in 3 pages.
International Preliminary Report on Patentability in PCT Application No. PCT/US2017/057725 dated May 2, 2019 in 10 pages.
International Preliminary Report on Patentability in PCT Application No. PCT/US2017/057712 dated May 2, 2019 in 9 pages.
Official Communication received in U.S. Appl. No. 16/185,399 dated Apr. 2, 2019 in 24 pages.

(56) References Cited

OTHER PUBLICATIONS

International Search Report in PCT Application No. PCT/US2018/059890 dated Jan. 23, 2019 in 10 pages.
ARPA-E, "Portable Methane Detection System", dated Dec. 16, 2014 (including innovation update from May 2018) in 2 pages https://arpa-e.energy.gov/?q=slick-sheet-project/portable-methane-detection-system.
ARPA-E, "Wearable, Continuously Monitoring Methane Imagers", as updated Jan. 15, 2018 in 2 pages https://arpa-e.energy.gov/sites/default/files/Rebellion-MONITOR-May1.pdf.
Amendment After Allowance as filed in U.S. Appl. No. 15/471,398 dated Jan. 24, 2019 in 5 pages.
Notice of Allowance received in U.S. Appl. No. 14/571,398 dated Feb. 27, 2019 in 14 pages.
Notice of Allowance received in U.S. Appl. No. 14/571,398 dated Mar. 6, 2019 in 5 pages.
Notice of Allowance received in U.S. Appl. No. 15/462,352 dated May 23, 2019, 2019 in 10 pages.
Preliminary Amendment as filed in U.S. Appl. No. 16/138,823 dated May 23, 2019 in 5 pages.
Notice of Allowance received in U.S. Appl. No. 16/138,823 dated Jun. 14, 2019 in 10 pages.
Notice of Allowance received in U.S. Appl. No. 14/792,477 dated Jun. 21, 2019 in 10 pages.
Official Communication received in U.S. Appl. No. 15/166,092 dated Dec. 20, 2018 in 28 pages.
International Preliminary Report on Patentability in PCT Application No. PCT/US2018/019271 dated Sep. 6, 2019 in 11 pages.
Amendment as filed in U.S. Appl. No. 16/185,399 dated Jul. 2, 2019 in 7 pages.
Notice of Allowance received in U.S. Appl. No. 16/185,399 dated Jul. 26, 2019 in 9 pages.
Amendment as filed in U.S. Appl. No. 15/166,092 dated Jun. 20, 2019 in 10 pages.
Amendment as filed in U.S. Appl. No. 15/462,352 dated Aug. 21, 2019 in 5 pages.
Amendment as filed in U.S. Appl. No. 16/138,823 dated Nov. 14, 2019 in 6 pages.
Amendment as filed in U.S. Appl. No. 16/185,399 dated Nov. 27, 2019 in 3 pages.
Amendment as filed in U.S. Appl. No. 16/664,615 dated Jan. 16, 2020 in 5 pages.
Catanzaro, et al., "Design of Dual-Band SWIR/MWIR and MWIR/LWIR Imagers", Proceedings of SPIE 5406, Infrared Technology and Applications XXX, Aug. 30, 2004, pp. 829-835.
Extended European Search Report received in European Application No. 19170836.1 dated Aug. 16, 2019 in 12 pages.
King et al., "Airborne Scanning Spectrometer for Remote Sensing of Cloud, Aerosol, Water Vapor, and Surface Properties", Journal of Atmospheric and Oceanic Technology, Aug. 1996, vol. 13, No. 4, pp. 777-794.
Notice of Allowance received in U.S. Appl. No. 15/166,092 dated Oct. 18, 2019 in 19 pages.
Notice of Allowance received in U.S. Appl. No. 16/185,399 dated Nov. 7, 2019 in 8 pages.
Notice of Allowance received in U.S. Appl. No. 16/256,967 dated Feb. 18, 2020 in 7 pages.
Official Communication received in European Application No. 13732285.5 dated Sep. 10, 2019 in 6 pages.
Official Communication received in European Application No. EP 15165880.4 dated Jul. 5, 2019 in 4 pages.
Official Communication received in U.S. Appl. No. 15/902,336 dated Feb. 6, 2020 in 30 pages.
Official Communication received in U.S. Appl. No. 16/256,967 dated Oct. 2, 2019 in 12 pages.
Preliminary Amendment as filed in U.S. Appl. No. 16/256,967 dated Aug. 27, 2019 in 6 pages.
Preliminary Amendment as filed in U.S. Appl. No. 16/377,678 dated Nov. 21, 2019 in 4 pages.
Notice of Allowance and Fees Due (PTOL-85) dated Jul. 22, 2020 for U.S. Appl. No. 16/664,615.
Anonymous: "LeonardoDRS" Jan. 1, 2012 (Jan. 1, 2012), XP055683152 Retrieved from the Internet URL:https://www.leonardodrs.com/media/10437/2019_u8000_-mr- 2012-04-618_rev04.pdf.
Applicant-Initiated Interview Summary received in U.S. Appl. No. 14/792,477 dated Oct. 23, 2019, 3 pages.
Communication Pursuant to Rules 161(2) and 162 for European Application No. 18875450.1 dated Jun. 17, 2020, 3 pages.
Decision to Refuse dated Apr. 19, 2018 for EP Application No. 15165877.0.
EP Office Action dated Jan. 3, 2017 for EP Application No. 15165877.0, 9 pages.
European Search Report and Search Opinion Received for EP Application No. 17862635.4, dated May 13, 2020, 14 Pages.
European Search Report and Search Opinion Received for EP Application No. 17863243.6, dated Apr. 20, 2020, 8 Pages.
European search report dated Oct. 8, 2015 for EP Application No. 15165877.
Gao et al., "Snapshot Image-Mapping Spectrometer for Hyperspectral Fluorescence Microscopy", Optics and Photonics News, Nov. 2010, vol. 21, No. 12, p. 50.
International Preliminary Report on Patentability received for PCT Patent Application No. PCT/US2018/059890, dated May 22, 2020, 8 pages.
Non-Final Rejection dated Apr. 2, 2019 for U.S. Appl. No. 16/185,399.
Non-Final Rejection dated Jun. 1, 2020 for U.S. Appl. No. 16/530,232.
Notice of Allowance and Fees Due (PTOL-85) dated Jul. 6, 2020 for U.S. Appl. No. 16/138,823.
Notice of Allowance and Fees Due (PTOL-85) dated Jul. 26, 2019 for U.S. Appl. No. 16/185,399.
Notice of Allowance and Fees Due (PTOL-85) dated Jun. 14, 2019 for U.S. Appl. No. 16/138,823.
Notice of Allowance and Fees Due (PTOL-85) dated May 29, 2020 for U.S. Appl. No. 16/256,967.
Notice of Allowance and Fees Due (PTOL-85) dated Nov. 7, 2019 for U.S. Appl. No. 16/185,399.
Notice of Allowance received in U.S. Appl. No. 15/789,811 dated Mar. 27, 2019 in 9 pages.
Notice of Allowance received in U.S. Appl. No. 16/138,823 dated Mar. 12, 2020 in 28 pages.
Official Communication received in Canadian Application No. 2,873,989 dated Mar. 2, 2020 in 4 pages.
Official Communication received in U.S. Appl. No. 16/549,297 dated May 1, 2020 in 8 pages.
Official Communication received in U.S. Appl. No. 16/664,615 dated Apr. 9, 2020 in 9 pages.
Result of Consultation dated Feb. 27, 2018 for EP Application No. 15165877.0.
Summons to Attend Oral Hearing dated Oct. 10, 2017 for EP Application No. 15165877.0.
Annex to the communication dated Jan. 15, 2021 for EP Application No. 17862635.
Anonymous: "MikroScan 7200V", at least before Jul. 21, 2005 (Jul. 21, 2005), since cited in U.S. Patent Application Publication No. 2005/0156111, pp. 1-2, XP055763389, Retrieved from the Internet: URL:http://www.zycon.com/Literature/ 225306/71536/7200Vdatasheet.pdf [retrieved on Jan. 11, 2021].
Anonymous: "SD-12 Technical information Characteristics and use of infrared detectors", Jan. 1, 2011 (Jan. 1, 2011), pp. 1-43, XP055762489, Retrieved from the Internet: URL:https://www.hamamatsu.com/resources/pdf/ssd/ infrared_kird9001e.pdf [retrieved on Dec. 23, 2020].
Communication from the Examining Division dated Jan. 15, 2021 for EP Application No. 17862635.

\* cited by examiner

GAS IMAGING SYSTEM

CROSS-REFERENCE TO RELATED APPLICATIONS

This application claims the benefit of priority to U.S. Provisional Application No. 62/411,499, filed on Oct. 21, 2016, entitled "GAS IMAGING SYSTEM", and U.S. Provisional Application No. 62/427,109, filed on Nov. 28, 2016, entitled "GAS IMAGING SYSTEM," which are hereby incorporated by reference herein in their entirety.

BACKGROUND

Field

The present disclosure generally relates to a system and method for detecting and imaging the concentration of various types of substances (e.g., gases), including hydrocarbons.

Description of the Related Technology

Spectral imaging systems and methods have applications in a variety of fields. Spectral imaging systems and methods obtain a spectral image of a scene in one or more regions of the electromagnetic spectrum to detect phenomena, identify material compositions or characterize processes.

Various spectral imaging systems currently available may be limited by a number of factors. For example, to increase sensitivity, various spectral imaging systems may require cryogenic cooling of the sensor element (e.g., optical detector array). This can substantially increase the cost, mass, power consumption, and complexity of the imaging system. Furthermore, it may not be practical to use various spectral imaging systems that employ cryogenic cooling in situations where a hand-held or battery-operated device is desired. Furthermore, various spectral imaging systems available today may not be capable of providing imaging with adequate sensitivity, specificity or resolution.

SUMMARY

The systems, methods and devices of this disclosure each have several innovative aspects, no single one of which is solely responsible for the desirable attributes disclosed herein. Each of the embodiments disclosed herein can be used in conjunction with the systems and methods disclosed throughout U.S. Pat. No. 9,756,263 (entitled "MOBILE GAS AND CHEMICAL IMAGING CAMERA), filed on Apr. 30, 2015; and throughout U.S. Patent Publication No. U.S. 2016/0349228 (entitled "HYDROGEN SULFIDE IMAGING SYSTEM), filed on May 26, 2016, the entire contents of each of which are hereby incorporated by reference herein in their entirety and for all purposes.

The present disclosure relates to spectral imaging systems. Some embodiments provide high-resolution imaging of a target substance, such as methane, by measuring the absorption signal in more than one band of the infrared spectrum. Other embodiments can provide high-resolution imaging by obtaining spectral measurements comprising the absorption signal of a target substance, and measurements not comprising the absorption signal, and combining the measurements.

Some spectral imaging systems can detect and visualize the distribution of volatile substances, for example to visualize the distribution of gases, such as methane, in air. The unintentional release of gases, such as methane, from oil wells or processing plants, for example hydrocarbon refineries, is a persistent problem and poses a safety hazard to humans, an explosion hazard, and adverse environmental effects. As such, spectral imaging systems that can detect, quantify and track the distribution of gases such as methane with high temporal and spatial resolution are useful to detect an unintentional release of a gas, to determine the escaping quantity, pinpoint the source and to verify that any remedial action has been effective. Other applications for spectral imaging systems include flame detection and determination of combustion efficiency.

In contrast to cryogenically cooled systems, various embodiments disclosed herein do not require cooling. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin. For example, in various implementations, the imaging systems disclosed herein do not include a cooler for cooling the detectors to a temperature below 300 Kelvin. As another example, in various implementations, the imaging systems disclosed herein do not include a cooler for cooling the detectors to a temperature below 273 Kelvin. As yet another example, in various implementations, the imaging systems disclosed herein do not include a cooler for cooling the detectors to a temperature below 250 Kelvin. As another example, in various implementations, the imaging systems disclosed herein do not include a cooler for cooling the detectors to a temperature below 200 Kelvin.

Partly because of their lower complexity and power requirements, various embodiments as disclosed herein may be manufactured at lower cost than conventional systems, and may be manufactured in a smaller form factor. Various embodiments disclosed herein can be manufactured in a form factor that is sufficiently small for the device to be easily man-portable or even wearable. For example, some embodiments may be designed for portable use and may encompass system dimensions of less than 3 in×3 in×1.5 in. Other embodiments may be designed for stationary use, such as for permanent installation near an oil well or a hydrocarbon refinery for leak detection. Various embodiments configured for stationary use may have dimensions less than or equal to about 20 in×30 in×15 in, 20 in×20 in×20 in, 2 ft×3 ft×1 ft or 2 ft×3 ft×1.5 ft or in any range between these dimensions.

Partly because of their lower complexity and power requirements, various embodiments disclosed herein may be operated from a battery, for example a rechargeable lithium-ion (Li-ion), nickel-metal hydride (NiMH) or nickel-cadmium (NiCD) battery. For some embodiments, the life of the battery between re-charges may exceed 8 hours of operation.

Various spectral measurement systems may be limited to only measuring the characteristics of the absorption signal in either the longwave infrared (LIR) or the midwave infrared (MIR) regions of the spectrum. Because they do not simultaneously take into account more than one band of the absorption signal, their sensitivity and noise characteristics provide ineffective imaging of the target substance. For example, some environmental conditions, (e.g., the sun being low on the horizon, presence of pollutants/chemicals in the air, etc.) may cause interference in detecting/identifying spectral peaks of chemical species of interest in a certain spectral region thereby making detection/identification of spectral peaks impractical. In this situation, a spectral imaging system measuring only inside a certain spectral region may not be able to capture adequate levels of the absorption signal and thus not perform adequately. In contrast, the embodiments of spectral imaging systems as disclosed herein can be configured to obtain spectral measurements in more than one spectral region. Accordingly, the embodiments of spectral imaging systems as disclosed herein can have superior performance as compared to various spectral imaging systems that are configured to obtain spectral measurements in only a certain spectral region.

Many chemical substances have characteristic absorption regions or peaks in the infrared spectrum that can be used to determine their presence and concentration by measuring the spectrum of light passing through them. For example, methane features one characteristic absorption region or peak between 3000 nm and 3500 nm and another between 7500 nm and 8000 nm (or between 7000 nm and 8500 nm). Light travelling through the substance may thus be attenuated in the characteristic absorption regions of the substance, with the amount of attenuation depending on the concentration of the substance. An absorption region or peak of a substance may be characterized by various parameters that are characteristic of the substance, including a characteristic wavelength of the peak (e.g. the wavelength associated with maximum absorption, or a spectral centroid wavelength of the peak), and/or a width of the peak (e.g. full width at half maximum, half width at half maximum). Such characteristics and regions may be monitored to detect the presence of a substance such as a gas.

Moreover, this approach can be utilized to measure the concentration of a substance by measuring the spectral power in one or more of the absorption regions. In various embodiments, optical detection and characterization of the substance can be accomplished by selecting spectral regions characteristic for the substance to be measured, filtering an incoming signal to attenuate spectral components falling outside of the selected spectral regions, and measuring the power of the remaining signal. Filtering the incoming signal to attenuate the undesired spectral components may be accomplished by placing filters in the light path between the objective and the sensor element (e.g., optical detector array), for example absorption filters, interference filters, and Fabry-Perot etalon based filters, to name just a few. Filtering the incoming signal to attenuate the undesired spectral components may have additional advantages such as for example, reducing computational load during processing the obtained spectrum, increasing signal-to-noise ratio, etc. The attenuation of spectral components outside the selected spectral region may depend on the materials and/or configuration of the filter. In various embodiments, spectral components outside the selected spectral region may be attenuated between, e.g., 3 dB and 50 dB, e.g., by about 3 dB, 4 dB, 6 dB, 10 dB, 20 dB, 30 dB, 40 dB or 50 dB relative to spectral components inside the selected spectral region. Similarly, spectral components outside the selected spectral region may be attenuated by any amount in any range between any of these values.

Because the spectral responsivity of the overall system is determined by the convolution of the spectra of all filters placed before the sensor element (e.g., optical detector array), and the responsivity spectrum of the sensor element itself, it is useful for the purposes of the instant disclosure to refer to the filters and sensor element together as a whole as an optical detection unit.

By using a sensor element that comprises multiple pixels, the spectral power measurement can be spatially resolved. This allows for a visual map of the concentration to be created, thus permitting the user to see the concentration and observe its variation over time and space. In various embodiments, the sensor element can include a CCD sensor (e.g., CCD sensor array), a CMOS sensor (e.g., CMOS sensor array), a bolometer (e.g., a bolometer array), a microbolometer (e.g., a microbolometer array) or another type of detector (e.g., detector array) that is sensitive to infrared radiation. In various embodiments, the sensor element can be designed as a Focal Plane Array (FPA). In various embodiments, the sensor element can comprise a focal plane array including a plurality of cameras. In some embodiments, the sensor element can include a two-dimensional array of infrared detectors.

Without any loss of generality, the ratio of the power of the received signal to the average power of the system noise can be referred to as signal-to-noise ratio. The signal-to-noise ratio can limit the maximum resolution of the imaging system spatially, temporally and/or with respect to concentration. Accordingly, it is desirable to configure spectral imaging systems to have increased signal-to-noise ratio. Without any loss of generality, signal-to-noise ratio can be increased by depressing the power of the noise and/or amplifying the signal.

Thermal noise contributes to the overall noise of the system and can be reduced by cryogenic cooling of the sensor element, thus improving the signal-to-noise ratio. Cryogenic cooling, however, typically utilizes a cooling apparatus that increases cost, size, complexity and mass of the system and is thus particularly undesirable in handheld or battery-powered devices. The signal-to-noise ratio can also be improved by amplifying the signal. In some embodiments, the signal may be amplified increasing the active area of the pixels in the sensor element.

Spectral imaging systems exist that only measure the absorption peak in one spectral region. The power of the signal that can be measured can thus be limited to the power of the absorption peak in that one region. An example conventional imaging system featuring a cryogenically cooled InSb sensor may achieve a signal-to-noise ratio of 8.5 dB.

As discussed above, some embodiments disclosed herein can beneficially be configured to obtain spectral characteristics of a chemical species in more than one spectral region. For example, the embodiments discussed herein are configured to obtain spectral measurements of a target chemical species (e.g., methane) in the mid-wave infrared region from about 3100 nm to 3900 nm, as well as in the long-wave infrared region between 7000 nm and 8000 nm (or 7000 nm to 8500 nm, or 7000 nm to 8300 nm). For example, the embodiments discussed herein can obtain spectral measurements of a target species in a spectral range between about 3000 nm and about 4000 nm, between about 3000 nm and about 3850 nm, between about 3150 nm and about 3850 nm, between about 3200 nm and about 3800 nm, between about 3300 nm and about 3700 nm, between about 3400 nm and about 3600, between about 3450 nm and about 3550 nm or at any wavelength in these range or sub-ranges (e.g., any range between any of these values). As another example, the embodiments discussed herein can obtain spectral measurements of a target species in a spectral range between about 7000 nm and about 8500 nm, between about 7000 nm and about 8300 nm, between about 7050 nm and about 7950 nm, between about 7100 nm and about 7900 nm, between about 7200 nm and about 7800, between about 7300 nm and about 7700, between about 7400 nm and about 7600, between about 7450 and about 7550 or at any wavelength in these range or sub-ranges (e.g., any range between any of these values). As a specific example, some embodiments may be most sensitive to the peak at 7600 nm and the peak at 3200 nm or thereabouts. Other embodiments may be most sensitive to the peak at 7400 nm and the peak at 3400 nm or thereabouts. Still other embodiments may be most sensitive to the peak at 3300 nm and the peak at 7700 nm or thereabouts. It is noted that the embodiments of the spectral imaging systems discussed herein can be configured to obtain spectral measurements outside the spectral range between 3100 nm and 3900 nm or the spectral range between 7000 nm and about 8000 nm. For example, depending on the chemical species of interest, the embodiments of the spectral imaging systems can be configured to obtain spectral measurements in any mid-infrared spectral region (between about 3 microns and about 7 microns) and long-infrared spectral region (between about 7 microns and about 16 microns).

Increasing the number of measured peaks can increase the power of the measured absorption signal. The embodiments of the spectral imaging systems configured to obtain spectral measurements in more than one spectral region may be configured to achieve a signal-to-noise ratio greater than or equal to about 9.5 dB without utilizing active cooling of the sensor element. For example, the systems described herein can be configured to have a signal-to-noise ratio between about 9.5 dB and about 50 dB, between about 10.5 dB and about 45 dB between about 11.5 dB and about 40 dB, between about 12.5 dB and about 35 dB, between about 15 dB and about 30 dB, between about 20 dB and about 25 dB or values in these ranges or sub-ranges (e.g., any range between any of these values). Various embodiments of the systems described herein can be configured to have a signal-to-noise ratio greater than 50 dB (e.g., 60 dB, 75 dB, 100 dB, etc. or any value in any range between any of these values). It will be appreciated that some embodiments as disclosed herein may achieve even higher signal-to-noise ratios; for example, some embodiments may utilize active cooling of the sensor element and achieve signal-to-noise ratios of 10.5 dB. Other embodiments may encompass other design elements, such as higher detector area, thus achieving signal-to-noise ratios such as 11.5 dB or even higher.

Some environmental conditions may render the operation of some spectral imaging systems difficult or impossible. For example, spectral imaging systems generally perform worse when the thermal contrast of the scene is low, such as in conditions of high ambient temperatures. Similarly, when imaging an outdoor scene during dusk or dawn, the low-standing sun can make the operating of an imaging system more difficult. In those situations, it may be particularly advantageous to capture a stronger signal by measuring absorption peaks from more than one region to compensate for the increase in noise. Accordingly, various embodiments of spectral imaging systems discussed herein can be used in environments in which other imaging systems that are based on exclusively measuring one spectral region could not be used.

The sensor response that corresponds to a given spectral power may vary based on various environmental factors including but not limited to the ambient temperature of a sensor element. For example, all other factors being equal, a higher sensor temperature may lead to a smaller sensor response for the same amount of absorbed spectral power. Other factors, such as lens vignetting, may also change the sensor response.

As such, it may be desirable to calibrate the sensor element by observing the response of the sensor element to a test signal with known spectral characteristics and recording this observation. This information can be used during measurement of a scene to determine what spectral power a given sensor element response corresponds to. For example, a gain value and an offset value may be determined for each pixel of the sensor element to establish a correspondence between the measured sensor element response and the test signal.

This may be accomplished by blocking the sensor with a shutter, such as a black-body or grey-body test object, or controlled-temperature bodies. The shutter may be implemented by using an electric motor by rotating a shutter element mounted on the motor axis so as to block and unblock the light path as desired. Alternatively, calibration may be performed manually, for example by the system prompting the user to manually block and unblock the light path, for example by putting a lens cap in front of the objective for calibration and removing it when calibration is complete. Alternatively, calibration may be performed during manufacturing by observing the response from the sensor when exposed to a known test signal.

This calibration may be repeated upon user request, or automatically, for example, upon determination of the system that the operating characteristics of the sensor element, such as the sensor element temperature, have changed sufficiently to require re-calibration.

In some embodiments, it may be desirable to include more than one sensor element; for example, to measure different spectral regions of the scene. In some embodiments, two sensor elements are used to measure the scene both including and excluding the absorption signal. In some embodiments, these two measurements are then processed by taking the difference. This may be accomplished using an algorithm implemented on a digital processor, or using analog circuitry or other electronics. Gaining information about the scene both with and without the absorption signal may be advantageous for several reasons: In some embodiments, the additional information may allow for a more accurate quantification of the absorption signal and a more reliable exclusion of false positives. In some embodiments, the imaging system may be capable of positively identifying the presence and source of a target substance with good accuracy without human assistance.

Some embodiments may measure and store the temperature of the sensor element, at which calibration was performed, in computer memory. Some embodiments may run the calibration process during start-up. In some embodiments, the system can be configured to, periodically, for example every minute, compare the difference between the stored temperature and the current temperature. If the difference exceeds a pre-determined threshold, (e.g., ±10 degree Kelvin, ±5 degree Kelvin, ±4 degree Kelvin, ±3 degree Kelvin, ±2 degree Kelvin, ±1 degree Kelvin, etc.), the calibration process can be repeated. If the difference does not exceed such pre-determined threshold, the system can be configured to take no action is taken. Accordingly, in various implementations, the calibration can be performed frequently enough to control the errors induced by temperature drift, while avoiding unnecessary calibration cycles.

In some embodiments, the sensor element (e.g., optical detector array) can be thermally connected to a thermo-electric cooler. The thermo-electric cooler may be linked to a control loop configured, for example, to hold the temperature of the sensor element since the last calibration. This allows for errors caused by temperature drift to be reduced.

In some embodiments, this functionality may be adjustable to allow the user to determine the desired trade-off between power consumption and noise performance. For example, the user may, upon start-up, be prompted to determine a target temperature to which the sensor element is cooled. The user may increase the measurement accuracy by selecting a low target temperature (which may reduce noise), or may choose to reduce or minimize energy consumption by selecting a higher target temperature. The user may also be given the option to turn off the thermo-electric cooler altogether, thus operating the sensor element at ambient temperature and minimizing energy consumption.

In some embodiments, the filters passing only the desired spectral regions may be mounted to be interchangeable, such as in a filter cassette, so as to allow the system to be used for measuring different substances by mounting the corresponding filter. For example, the filter cassette may be designed so as to allow manual or automatic rapid interchange between filters.

In some embodiments, the objective lens may be interchangeable, so as to allow the system to accommodate different lenses to allow the user to vary parameters such as field-of-view or detection range. The objective lens may be of fixed focal length, or allow for different focal lengths, so as to allow the user to optically zoom in and out of the scene. For example, in one embodiment, the focal length of the objective lens may be fixed at 25 mm. In other embodiments, the focal length of the objective lens may be continuously variable between about 20 mm and about 45 mm.

In some embodiments, imaging of the scene may be performed by more than one FPA. In various embodiments, for example, two FPAs are used, and a dichroic beamsplitter is used to divide the incoming light between the two FPAs. Different filters can be placed in the light path before each FPA. The filters placed before the first FPA can be configured so as to pass the spectral regions containing the absorption signals, and the filters placed before the second FPA can be configured to filter out those spectral regions. The absorption signal can be calculated by the difference in signal from the first and the second FPA. Embodiments featuring more than one FPA may have several advantages over embodiments only using one; for example, the difference measurement allows the system to isolate the absorption signal from the target substance, such as methane, more accurately. In one embodiment, for example, the filter configuration of the first FPA may be transmissive (e.g., selectively transmissive) to the radiation in the mid-wave infrared region from about 3100 nm to 3900 nm (e.g., between about 3150 nm and about 3850, between about 3200 nm and about 3800, between about 3300 nm and about 3700, between about 3400 nm and about 3600, between about 3450 nm and about 3550 or at any wavelength in these ranges or sub-ranges, e.g., any range formed by any of these values), and to radiation in the long-wave infrared region between 7000 nm and 8000 nm (e.g., between about 7050 nm and about 7950, between about 7100 nm and about 7900, between about 7200 nm and about 7800, between about 7300 nm and about 7700, between about 7400 nm and about 7600, between about 7450 and about 7550 or at any wavelength in these ranges or sub-ranges, e.g., any range formed by any of these values), while the filter configuration of the second FPA may be configured to transmit (e.g., selectively transmit) radiation outside these ranges (e.g., between about 1-3 micron, between about 4-6 micron and/or between about 8-16 micron).

Some embodiments provide an infrared (IR) imaging system for detecting methane gas. In some embodiments configured to detect methane, the imaging system can include an optical filter cascade comprising two filters. A first filter selectively passes light having a wavelength of less than, for example, 8500 nm, 8300 nm, 8200 nm or 8400 nm or thereabouts, while attenuating light at wavelengths at or above that threshold to a second filter. The second filter then selectively passes light with a wavelength in another range, for example, in a range above 3000 nm and below 4000 nm, in a range above 3200 nm and 3900 nm or in a range above 3100 nm and below 4100 nm, or thereabouts, and in another range, for example in a range above 6000 nm and below 8500 nm, or above 6200 nm and below 8400 nm, or above 5800 nm and below 8300 nm, or thereabouts, to the sensor element. In various embodiments, a notch filter can be used.

The responsivity of the optical detection unit can then determined based on the convolution of the filter transmission spectra with the sensor element responsivity. By matching a suitable sensor element configuration to suitable filters, it is possible to concentrate a high fraction of the spectral power of the optical detection unit responsivity in the absorption regions around 3500 nm and 8000 nm. In an embodiment of the spectral imaging system configured to detect methane, the sensor element configuration can be chosen so as to have an increased or maximum responsivity in the areas around 3500 nm and 8000 nm or thereabouts, so as to capture the two strong absorption peaks of methane in conjunction with suitably chosen filters.

Accordingly, in various embodiments, an infrared (IR) imaging system for detecting a substance that has one or more infrared absorption peaks is disclosed. The imaging system can include an optical detection unit, including an optical detector array. The optical detector array can have increased sensitivity in a spectral range corresponding to at least one of the one or more infrared absorption peaks and one or more optical filters configured to selectively pass light in the spectral range.

In another embodiment, an infrared (IR) imaging system with an optical detection unit having a single optical channel is disclosed. The convolution of the responsivity function of an optical detector array of the optical detection unit and a transmissive filter of the optical detection unit may be non-zero in spectral regions corresponding to the peaks in the absorption spectrum of a target species, and in some implementations, may selectively attenuate other wavelengths outside those spectral regions corresponding to the peaks in the absorption spectrum of a target species such as spectral regions adjacent those spectral ranges corresponding to the peaks in the absorption spectrum of a target species.

In yet another embodiment, a spectral imaging system is disclosed. The spectral imaging system can include a first optical detecting unit comprising a first optical detector array configured to capture a first image of the scene, where the first optical detector array is configured to have increased sensitivity to one or more wavelengths in a first spectral range. The system can also include a second optical detecting unit comprising a second optical detector array, configured to capture a second image of the scene, with the second optical detector array configured to have increased sensitivity to one or more wavelengths in a second spectral range. In various embodiments, the first spectral range may comprise regions in one or more of the short-wave infrared, mid-wave infrared, or long-wave infrared region such as the mid-wave infrared. In some embodiments, the second spectral range may comprise regions in one or more of the short-wave infrared, mid-wave infrared, or long-wave infrared region such as the long-weave infrared regions. In some implementations, the system may further include processing electronics configured to identify a target species based on the first and the second image, determine a concentration of the identified target species based on the first and the second image, or both. Alternatively, or in addition, in some implementations, the system may further include processing electronics and a display configured to display an image based on a comparison of the first and second images.

Accordingly, in various embodiments, the second spectral range may comprise regions in one or more of the short-wave infrared, mid-wave infrared, or long-wave infrared region, and may or may not overlap with the first spectral range. In certain embodiments, the imaging system may be configured and the first spectral range and second spectral range may be selected for the system to image methane.

In various embodiments, an optical detection unit may have a single optical channel, configured so that a convolution of a responsivity function of an optical detector array of the optical detection unit and a transmissive filter of the optical detection unit may be non-zero and/or comprise peaks in spectral regions corresponding to the peaks in the absorption spectrum of a target species (e.g. methane).

The optical detector array may comprise active sub-elements, such as an infrared detector array, a micro-bolometer array, a bolometer array, a camera or an imaging element. In an embodiment, the optical detector array (or an active sub-element such as a microbolometer array or infrared detector array, camera, or imaging element) may be configured to be cooled by a thermos-electric cooler. In another embodiment, no cooler may be provided and the optical detector array is not configured to be cooled below an ambient or operating temperature (e.g. 300K, 350K, 380K or above). In an embodiment, only passive cooling, such as a heat sink or fin, may be used for cooling the optical detector array.

In some embodiments, a method of imaging a scene is disclosed. The method can include obtaining a first measurement of the scene in a first spectral region, the first spectral region comprising a region corresponding to at least one infrared absorption peak of a substance. The method can include obtaining a second measurement of the scene in a second spectral region, the second spectral region different from the first spectral region. The method can include determining a concentration of the substance.

In an embodiment, the first spectral region may be in a range between about 3000 nm and 4000 nm, between about 6000 nm and about 8300 nm, between about 3200 nm and about 3400 nm, between about 7200 nm and about 7800 nm, between about 3000 nm and about 3500 nm, between about 7000 nm and about 7600 nm, between about 3350 nm and about 3450 nm, between about 7000 nm and about 7900 nm or any wavelengths in these ranges/sub-ranges (e.g., any range formed by any of these values). The one or more optical filters may be configured to selectively pass radiation in the first spectral range and the second spectral range. In an embodiment, the one or more optical filters comprises a short-pass filter configured to transmit radiation in the wavelength region between 3-8.3 microns. The optical detector array has increased sensitivity in a first spectral range between 3-4 microns and a second spectral range between 7-8 microns. The optical detector array may have decreased sensitivity in another range or region, e.g. between 4-6 microns. The system may be configured to be portable (e.g. handheld) and/or battery operated. In an embodiment, the system may further comprise a display, such as an liquid-crystal display, configured to render a detected quantity, plume or concentration of a target substance (e.g. methane) on the screen. The system may further be configured to periodically, e.g. in real-time (e.g. 5 times per second, 10 times per second, 25 times per second) refresh the output on the screen based on a new measurement to provide a real-time or near real-time display output.

In some embodiments, the first optical detection unit and the second optical detection unit correspond to first and second optical channels for imaging, and the first and second optical imaging channels may be used to identify the target species without any additional optical imaging channels. The second optical detecting unit may have decreased sensitivity to the first spectral range, and the first optical detecting unit has decreased sensitivity to the second spectral range.

In some embodiments, an infrared imaging system is configured to detect and identify a target species (e.g. methane) associated with an absorption spectrum. The spectral imaging system may include a first optical detecting array configured to detect infra-red radiation, the optical detecting array characterized by a spectral response curve defining a responsivity of the optical detection unit to IR radiation across a range of wavelengths, and wherein a convolution of the spectral response curve with the absorption spectrum of the target species defines a first peak at a first wavelength and a second peak at a second wavelength different from the first wavelength. There may be an attenuated region between the first peak and the second peak, wherein in the spectral curve, the first peak is higher (e.g. two times, five times, ten times, 50 times) higher than a wavelength in the attenuated region. In an embodiment, the first wavelength may be in a range of 3 microns to 4 microns; in another embodiment, the second wavelength may be in a range of 6 microns to 8 microns. The optical detection unit may comprise one or more optical filters configured to selectively pass light in the range of wavelengths. The spectral response curve of the optical detection unit may be characterized by a convolution of the responsivity of the optical detector array and the transmission spectrum of the one or more optical filters. The system may comprise a single optical channel for imaging.

In some embodiments, a second non-target species (e.g. water) may be associated with a second absorption spectrum, wherein a convolution of the spectral response curve with the second absorption spectrum is less than the convolution of the spectral response curve with the absorption spectrum of the target species. The convolution in the non-zero spectral regions corresponding to the peaks may be greater (e.g. at least 2 times greater, at least 5 times greater, at least 10 times greater, at least 15 times greater) than the convolution in other spectral regions not corresponding to the peaks. The convolution in the non-zero spectral regions corresponding to the peaks may be greater than the convolution in every other spectral region.

In yet another embodiment, the system may be configured to detect infrared image data at wavelengths less than 8 microns, or at less than 9 microns, and may be configured to process the detected infrared image data to identify the target species.

In yet another embodiment, a method of imaging a scene is disclosed. The method can include obtaining a first measurement of the scene in a first spectral region that comprises a region corresponding to at least one infrared absorption peak of a substance, obtaining a second measurement of the scene in a second spectral region that is different from the first spectral region, and determining a concentration of the substance.

In yet another embodiment, an infrared (IR) imaging system for detecting a substance that has one or more infrared absorption peaks is disclosed. The imaging system can include an optical detection unit, including an optical detector array, and one or more optical filters that are configured to selectively pass light in a spectral range. A convolution of the responsivity of the optical detector array and the transmission spectrum of the one or more optical filters may have a first peak in mid-wave infrared spectral region between 3-4 microns corresponding to a first absorption peak of methane and may have a second peak in long-wave infrared spectral region between 6-8 microns corresponding to a second absorption peak of methane.

In yet another embodiment, an infrared (IR) imaging system for detecting and identifying a target species associated with an absorption spectrum is disclosed. The imaging system can include an optical detection unit, including an optical detector array configured to detect IR radiation. The optical detection unit can be characterized by a spectral response curve defining the responsivity of the optical detection unit to IR radiation across a range of wavelengths. A convolution of the spectral response curve with the absorption spectrum of the target species may define a first peak at a first wavelength and a second peak at a second wavelength different from the first wavelength.

DETAILED DESCRIPTION OF THE PREFERRED EMBODIMENT

Figure 1:
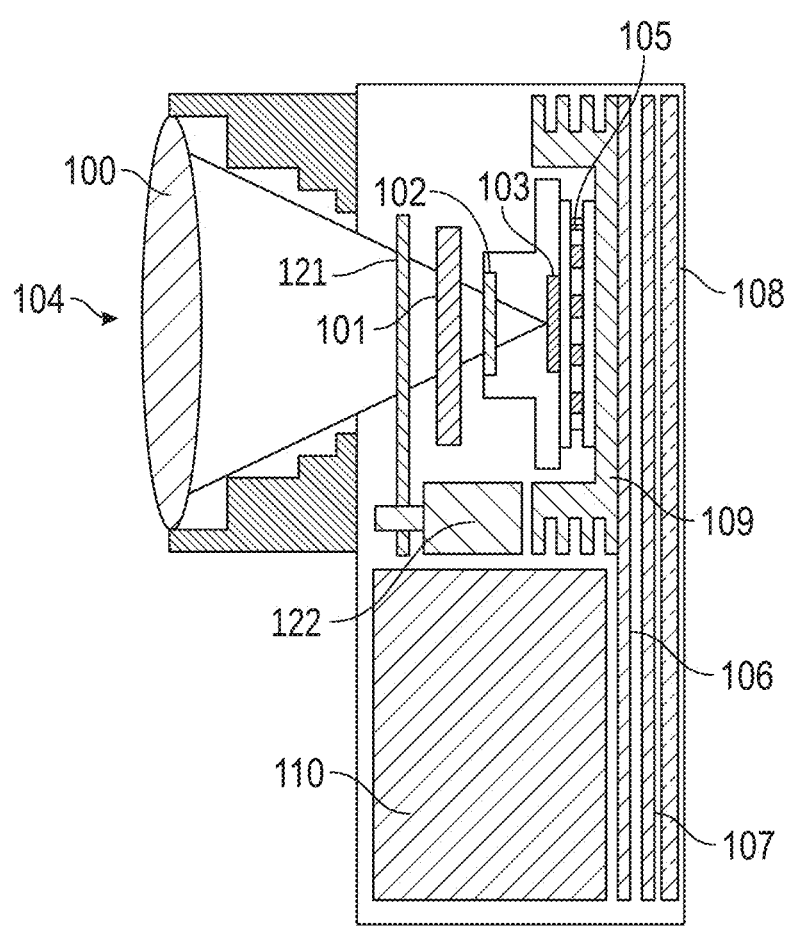
FIG. 1 is a schematic cross-sectional view of an imaging system according to various embodiments.

Reference will now be made to the drawings, in which like reference numerals refer to like parts throughout.

The following description is directed to certain implementations for the purposes of describing the innovative aspects of this disclosure. However, a person having ordinary skill in the art will readily recognize that the teachings herein can be applied in a multitude of different ways. The described implementations may be implemented in any device, apparatus, or system that can be configured to operate as an imaging system such as in an infra-red imaging system. The methods and systems described herein can be included in or associated with a variety of devices such as, but not limited to devices used for visible and infrared spectroscopy, multispectral and hyperspectral imaging devices used in oil and gas exploration, refining, and transportation, agriculture, remote sensing, defense and homeland security, surveillance, astronomy, environmental monitoring, etc. The methods and systems described herein have applications in a variety of fields including but not limited to agriculture, biology, physics, chemistry, defense and homeland security, environment, oil and gas industry, etc. The teachings are not intended to be limited to the implementations depicted solely in the Figures, but instead have wide applicability as will be readily apparent to one having ordinary skill in the art.

FIG. 1 illustrates an example of an imaging system according to various embodiments, such as may be used as a portable device by a worker in a hydrocarbon refinery for leak detection. In various embodiments, the device can be fixed or otherwise stationary so as to monitor the facility for leaks.

Light emitted or ambient light 104 reflected from an object, enters the imaging system through a front objective 100 which is configured to focus the light onto a focal plane array (FPA) 103. The FPA 103 can include a microbolometer (e.g., a microbolometer array). The light passes through a broadband filter 101, and then through a wideband filter 102 before entering the FPA 103. The wideband filter 102 can correspond to a transmissive window of the FPA 103.

In an example embodiment configured for the detection of methane, the wideband filter 102 may be configured to selectively pass light with a wavelength between about 3 microns and about 14 microns (e.g., above 3,000 nm and below 4,000 nm, and in a region above 6,000 nm and below 14,000 nm), while the broadband filter 101 may be configured to selectively pass light having a wavelength of less than 8300 nm while attenuating light at wavelengths at or above 8300 nm. In various embodiments, the sensor element and all other electronic components can be powered by a battery unit 110. In some embodiments, the battery unit 110 may comprise a rechargeable lithium-ion battery, or a compartment for single-use alkaline batteries.

The broadband filter 101, the wideband filter 102 and the optical FPA 103 can define an optical detection unit configured to pass and sense light in a plurality of predefined passbands, while having decreased sensitivity outside the plurality of predefined passbands. The predefined passbands can include wavelengths in a range between about 3000 nm and 4000 nm, between about 6000 nm and about 8300 nm, between about 3200 nm and about 3400 nm, between about 7200 nm and about 7800 nm, between about 3000 nm and about 3500 nm, between about 7000 nm and about 7600 nm, between about 3350 nm and about 3450 nm, between about 7000 nm and about 7900 nm or any wavelengths in these ranges/sub-ranges (e.g., any range formed by any of these values). In some embodiments, the optical detection unit can provide the predefined passbands with a plurality of filters in combination with the detector. In some embodiments, the optical detection unit can be configured such that the pixels of the sensor element are particularly sensitive to light within the predefined passbands.

With continued reference to FIG. 1, the FPA 103 varies a measurable electrical characteristic, such as resistance, with the incident power. The relationship between the measurable electrical characteristic and the incident power can be described by the FPA's calibration curve. The variation in electrical resistance can be measured by acquisition and control electronics 106 and converted into visual image data based on the FPA's calibration curve. In some embodiments, the acquisition and control electronics may be implemented using a general-purpose computer processor, or a field-programmable gate array (FPGA).

The visual image data can be processed by image processing electronics 107. For example, the image processing electronics 107 may perform interpolation between the measured pixels to create a smoother image. The image processing electronics may also perform different types of filtering and re-scaling, such as coloring the image based on a predetermined mapping between measured intensity and output color (the "color scheme"). In some embodiments, the image processing electronics may be implemented using a general-purpose computer processor, or a field-programmable gate array (FPGA). The image processing electronics can send the processed image data to a touch screen display 108 for output. The image processing electronics 107 and acquisition and control electronics 106 may allow the user to see and adjust configuration parameters through a touch screen display 108. Visible parameters may include the FPA 103 temperature, the estimated signal-to-noise ratio, the remaining battery life and the calibration status. Adjustable parameters may include the capture frame rate, the capture resolution and the color scheme. In some embodiments, the image-processing electronics may be configurable by the user to calculate the difference between a running average of a number of past measurements, for example 10, 15, 20, 36, 64, 128, or 256 past measurements, and the current measurement, thus emphasizing changes. This may aid the user in detecting a moving object, such as a gas cloud, against a stationary background.

To assist in determining the calibration curve, the system may comprise a motor-actuated shutter 121. One end of the shutter can be connected to the rotation axis of the motor 122 so that by spinning the motor the shutter can be moved in and out of the light path as desired. When the system is operating to determine the calibration curve, the shutter can be moved into the path between the front objective 100 and the FPA 103. This blocks substantially all incoming light and thus allows the FPA 103 to record a spectrum representing the emission spectrum of the shutter 121. From this measurement of a known spectrum, the FPA's calibration curve can be determined. When the system is operating in recording mode, the shutter 121 can be moved out of the path so as not to block incoming light.

The FPA 103 may be thermally coupled to a heatsink 109. The heatsink 109 may be mounted to the back side of the FPA, for example using thermal adhesive. The heatsink 109 may extend laterally around the FPA to provide for adequate and symmetric heat dissipation. The heatsink 109 may comprise fins to allow for increased convective heat dissipation. The FPA 103 may also be thermally coupled to a thermo-electric cooler 105, for example by attaching the FPA 103 to a heatsink or thermal conductor as described and then attaching, for example using thermal adhesive, a thermo-electric cooler to the back of the heat sink. The thermo-electric cooler can also be attached to a heat sink, such as the heat sink 109 shown having fins. If the FPA 103 is coupled to a thermo-electric cooler 105, the thermo-electric cooler may operate in a control loop to maintain the temperature at which the sensor element was last calibrated, thus reducing errors that are magnified by temperature differences between the temperature of the sensor element during calibration and during measurement. In still other embodiments, no thermo-electric cooler may be provided.

Figure 2:
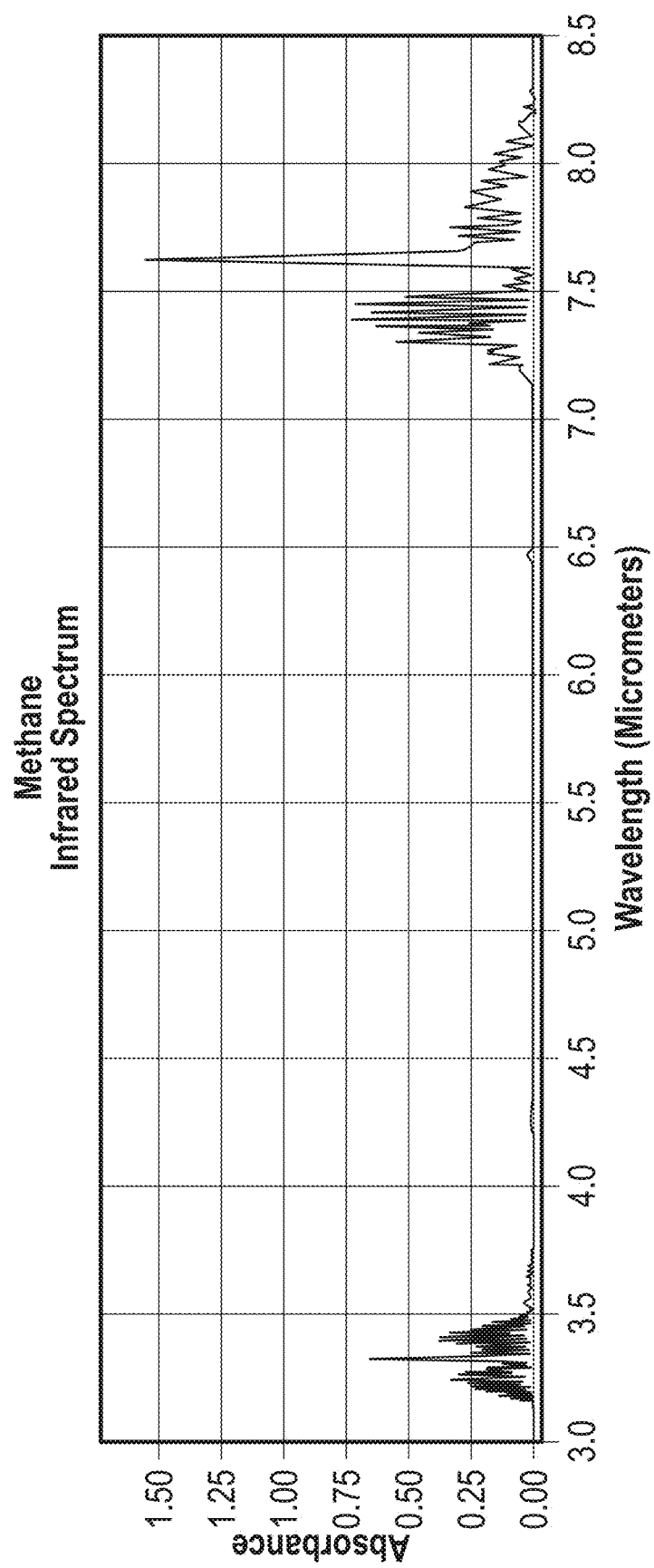
FIG. 2 is a plot illustrating the infrared absorption spectrum of methane, recorded in a wavelength range from 3000 nm to 8500 nm.

FIG. 2 shows the infrared absorption spectrum of methane. It will be appreciated that the absorption peaks of methane lie in both the mid-wave infrared and the long-wave infrared spectrum. As shown in FIG. 2, the absorption spectrum of methane includes significant absorption peaks in a range of 3 microns to 4 microns (e.g., in a range of 3 microns to 3.75 microns, or in a range of 3.1 microns to 3.75 microns), and in a range of 7 microns to 8.5 microns (e.g., in a range of 7 microns to 8.3 microns).

Figure 3A:
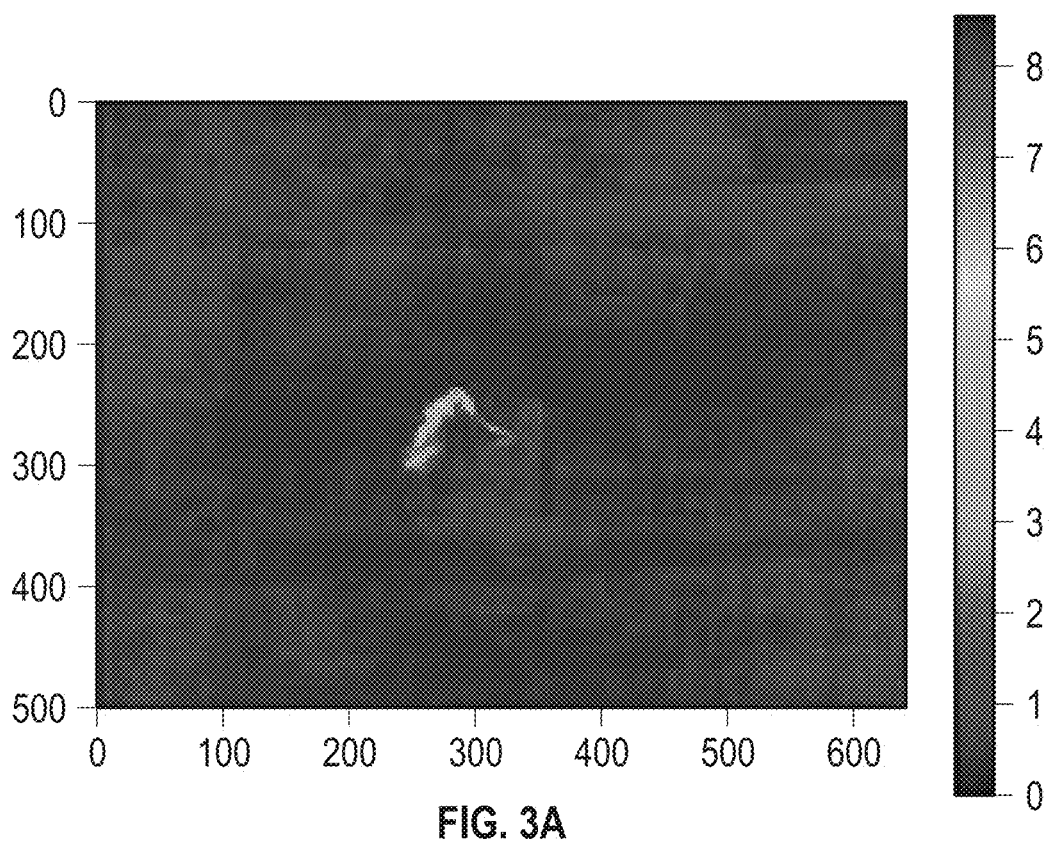
FIG. 3a is a snapshot image showing the absorption signal from a methane plume recorded from a distance of about 125 ft with an imaging system in accordance with the embodiments disclosed herein, shaded to indicate the signal-to-noise ratio.
Figure 3B:
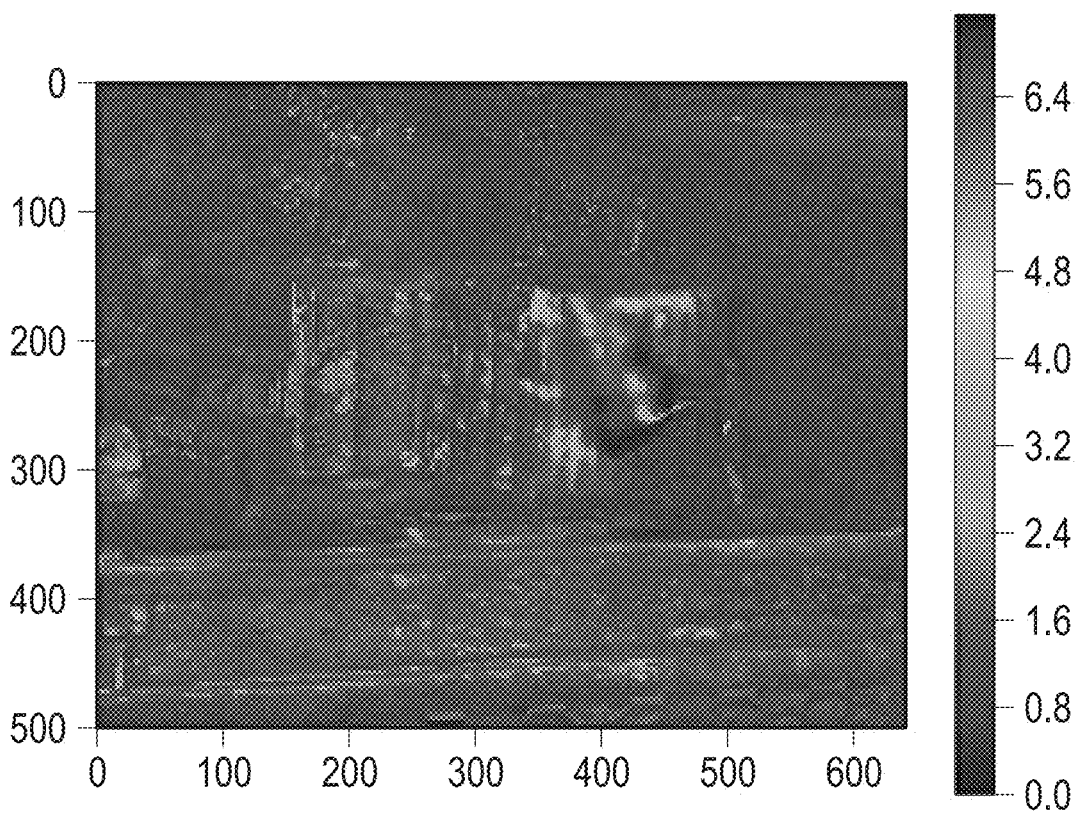
FIG. 3b is a snapshot image showing the absorption signal from a methane plume recorded from a distance of about 125 ft, shaded to indicate the signal-to-noise ratio, recorded with a cryogenically cooled imaging system presently available.

FIG. 3a and FIG. 3b both show recordings of a methane plume with spectral imaging systems recorded from a distance of about 125 ft. As indicated by the legend to the right of each figure, the shading of each pixel reflects the measured power of the pixel above the noise floor, i.e. the pixel's signal-to-noise ratio. The recording in FIG. 3a is from an embodiment of an imaging system as disclosed herein, measuring both the long-wave infrared and mid-wave absorption signals. The recording in FIG. 3b is from a presently available, cryogenically cooled imaging system, measuring only the mid-wave infrared absorption signal.

The power of the strongest measured absorption signal from the methane plume in FIG. 3a exceeds the power of the measured noise floor by a factor of 8. The power of the strongest measured absorption signal from the methane plume in FIG. 3b only exceeds the power of the measured noise floor by a factor of 6.4.

Figure 4:
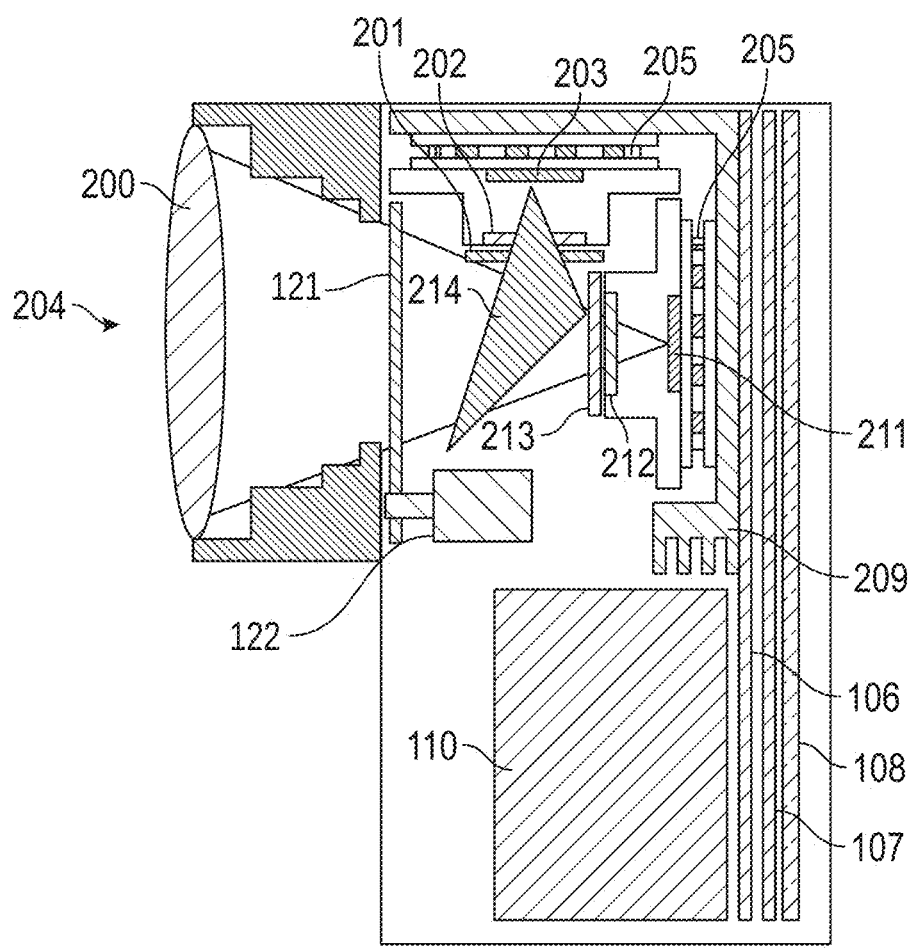
FIG. 4 is a schematic cross-sectional view of an imaging system, according to various embodiments disclosed herein.

FIG. 4 shows another embodiment of an imaging system as disclosed. Light emitted or ambient 204 reflected from an object, enters the imaging system through a front objective 200 and is split by a dichroic beamsplitter 214. The dichroic beamsplitter passes part of the light through a second broadband filter 213 and a second wideband filter 212 to a second FPA 211. The second wideband filter 212 can correspond to a transmissive window of the second FPA 211. The dichroic beamsplitter reflects part of the light to a first broadband filter 201 and a first wideband filter 202 to a first FPA 203. In some embodiments, the dichroic beamsplitter 214 can serve as and/or may replace one or more of the filters 201, 202, 212, 213 or assist in filtering. For example, the dichroic beamsplitter 214 may direct more light of a first spectral range to the first FPA and more light of a second spectral range to the second FPA so as to possibly assist in the wavelength filtering function.

The first FPA 203 can be used to form a first image of the object or scene. The second FPA 211 can be sued to form a second image of the object or scene. The first wideband filter 202 can correspond to a transmissive window of the first FPA 203. In some embodiments, the first FPA 203 may be configured to receive light containing the frequencies corresponding to the peaks in the absorption spectrum of the chemical species of interest, whereas the second FPA 211 may be configured to receive light outside the peaks in the absorption spectrum of the chemical species of interest. In various embodiments, the system can comprise processing electronics configured to compare the first and second images of the object formed by the first and second FPAs 203, 211. For example, in some embodiments, the processing electronics can be configured to identify the target species based on a calculated difference between the first image and the second image.

For example, in an embodiment configured to detect methane, the first wideband filter 202 may be configured to selectively pass light in a spectral range between 3-14 microns (e.g., with a wavelength above 3,000 nm and below 4,000 nm, and in a region above 6,000 nm and below 18,000 nm), while the first broadband filter 201 may be configured to selectively pass light having a wavelength of less than 8300 nm while attenuating light at wavelengths at or above 8300 nm (as shown by curve 501 of FIG. 5). The second wideband filter 212 may be configured to selectively pass light in the spectral region between about 4-6 microns and/or between about 8-16 microns, while the second broadband filter 213 may be configured to selectively pass light having a wavelength between about 8-16 microns (as shown by curve 503 of FIG. 5). In various embodiments, light having a wavelength at or below 8300 nm can be passed to the FPA 203, and light having a wavelength at or above 8300 can be passed to the FPA 211.

Thus, the embodiment of FIG. 4 can employ a two-channel imaging system for imaging two target species. The system of FIG. 4 can be used in conjunction with the systems and methods disclosed in U.S. Pat. No. 9,756,263 (entitled "MOBILE GAS AND CHEMICAL IMAGING CAMERA), filed on Apr. 30, 2015; and throughout U.S. Patent Publication No. U.S. 2016/0349228 (entitled "HYDROGEN SULFIDE IMAGING SYSTEM), filed on May 26, 2016, the entire contents of each of which are hereby incorporated by reference herein in their entirety and for all purposes.

Figure 5:
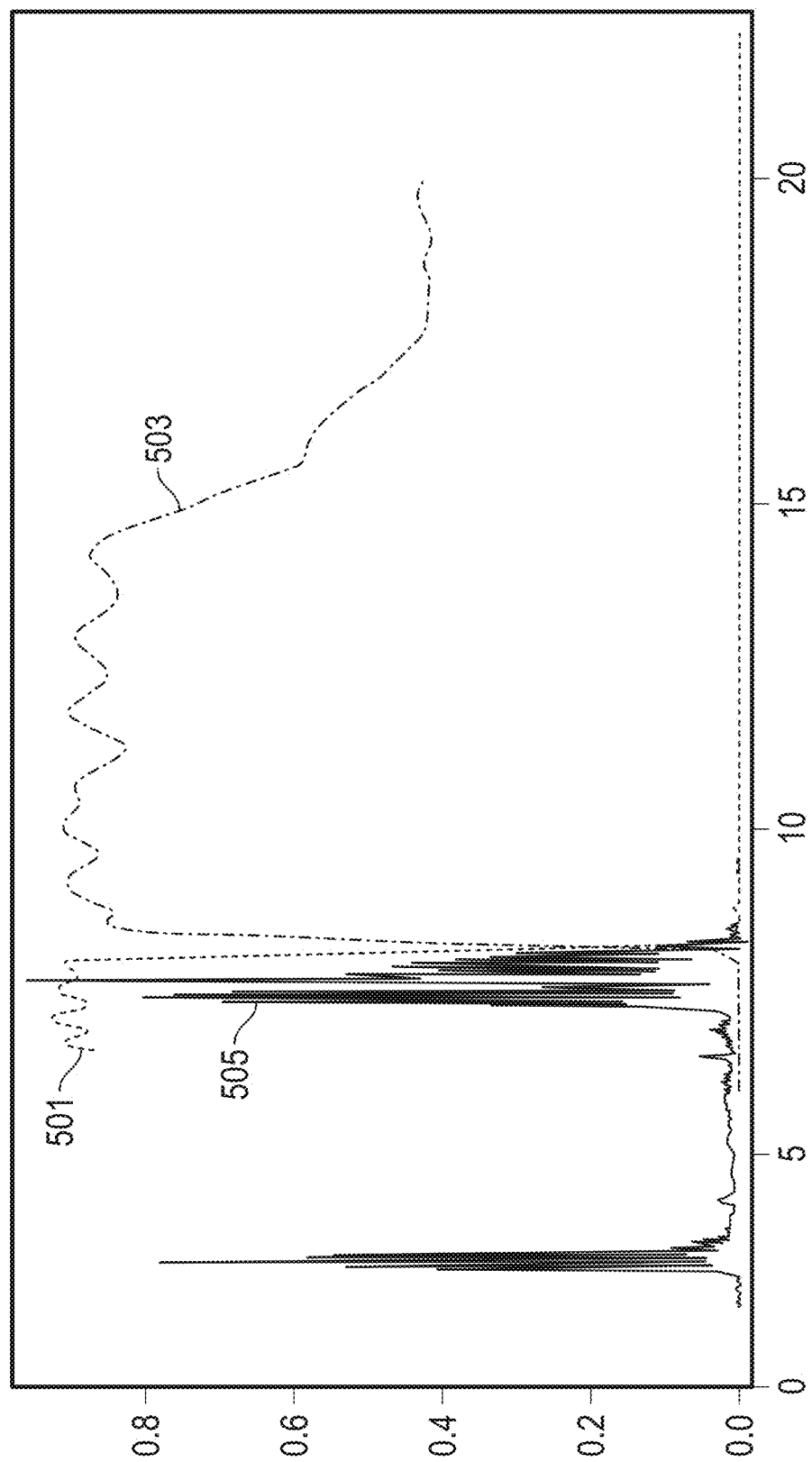
FIG. 5 shows the filter transmissivity functions according to some embodiments, and the infrared absorption spectrum of methane.

FIG. 5 shows a plot of several absorption spectra, with the x-axis being in units of microns. The spectrum shown in curve 505 indicates the absorption spectrum of methane. The spectrum shown in curve 501 indicates the transmission spectrum of a first filter (e.g. first broadband filter 201) that is placed before the first FPA 203, according to one embodiment. The spectrum shown in curve 503 indicates the transmission spectrum of a second filter (e.g. second broadband filter 213) that is placed before the second FPA 211, according to one embodiment. Substantially all of the absorption peaks of methane are transmitted to the FPA 203 by the filter placed before the first FPA 203, while substantially all of the absorption peaks of methane are filtered out by the filter placed before the second FPA 211. As disclosed herein, the first filter (e.g. first broadband filter 201) and second filter (e.g. second broadband filter 213) may be appropriately chosen with respect to the chemical species of interest. The first filter may be chosen to pass light corresponding to peaks in the absorption spectrum of the chemical species of interest, whereas the second filter may be chosen to attenuate light corresponding to those peaks.

Figure 6:
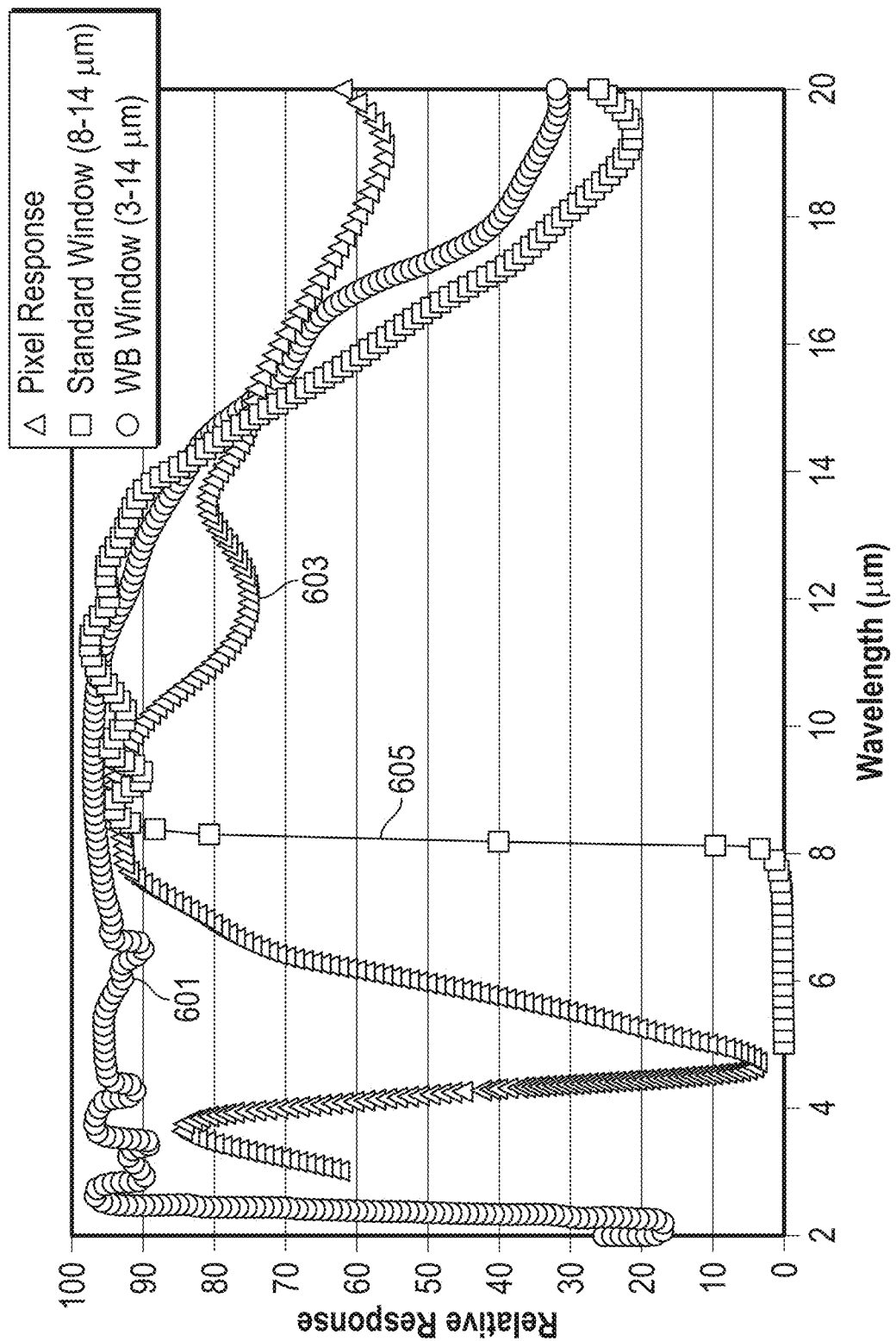
FIG. 6 shows the sensor element responsivity according to some embodiments and the transmission functions, as chosen by some conventional systems, and as chosen by some embodiments as disclosed herein, respectively.

FIG. 6 shows the spectral response of an embodiment of a sensor element and the transmissive windows associated with the sensor element. The spectrum shown in curve 601 indicates the transmission spectrum of a wideband (WB) transmissive window associated with an embodiment of a sensor element. The WB transmissive window can be configured as the wideband FPA filter, according to some embodiments as disclosed herein. The spectrum shown in curve 603 indicates the pixel response of the sensor element, according to some embodiments. The spectrum shown in curve 605 indicates the transmission spectrum of a standard transmissive window that is placed forward of the sensor element in various spectral imaging systems currently available in the market. It is noted that various spectral imaging systems currently available may not be capable of obtaining spectral measurements in the spectral range between about 2-8 microns as a result of decreased transmission in this range of the standard transmissive window. In contrast, the embodiments of spectral imaging systems discussed herein including a WB transmissive window having a transmission spectrum similar to the transmission spectrum depicted by curve 601 are capable of obtaining spectral measurements in the spectral range between about 2-8 microns. The convolution of the transmission spectrum of the WB transmissive window and the pixel response of the sensor element can yield a spectral response that has relatively increased response in spectral regions including and/or matching the peaks of the absorption spectra of methane, including the peak between 3000 nm and 3500 nm and the peak between 7000 nm and 8000 nm, for example, compared to surrounding spectral regions. The optical detection unit including the WB transmissive window and the sensor element can thus be sensitive to an absorption signal in these regions. Conversely, it will also be appreciated that, the standard transmissive window may eliminate substantially all of the absorption peaks of methane in the spectral region between 3000 nm and 3500 nm. Accordingly, the convolution between the standard transmissive window and the pixel response of the sensor element may be approximately zero, or otherwise negligible, in the area between 3000 nm and 3500 nm. The optical detection unit including a standard transmissive window may thus not be sensitive to an absorption signal in the region between 3000 nm and 3500 nm.

As discussed above, the convolution of the transmission spectrum 601 of the WB transmissive window and the pixel response 603 of the sensor element has peaks in the spectral region between 3-4 microns and between 7-8 microns and valleys between 1-3 microns and 4-6 microns. Accordingly, the embodiments of spectral imaging systems including a WB transmissive window and a sensor element having a pixel response similar to pixel response 603 are suitable to detect methane since they have increased sensitivity in the spectral region between 3-4 microns and between 7-8 microns—which corresponds to the absorption spectrum of methane. Such embodiments also have reduced interference from the water band (e.g., between 1-3 microns and 4-6 microns) since they have decreased sensitivity in the water band (e.g., between 1-3 microns and 4-6 microns). In various embodiments, a second sensor element (e.g., the second FPA 211 of FIG. 5) that is sensitive to radiation in the wavelength range between 8-16 microns can be used to detect vapor, steam or other chemical species.

Thus, in various embodiments, an optical detection unit can be characterized by a spectral response curve defining the responsivity of the optical detection unit to IR radiation across a range of wavelengths. A convolution of the spectral response curve with the absorption spectrum of the target species may define a first peak at a first wavelength and a second peak at a second wavelength different from the first wavelength.

In some embodiments, the convolution comprises an attenuated region between the first peak and the second peak, with the first peak at least five times as large as the attenuated region. In some embodiments, the first wavelength is in a range of 3 microns to 4 microns. The second wavelength can be in a range of 6 microns to 8 microns. In various embodiments, the target species comprises methane gas. In various embodiments, the optical detection unit can comprise an optical detector array and one or more optical filters configured to selectively pass light in the range of wavelengths. The spectral response curve of the optical detection unit can be defined characterized by a convolution of the responsivity of the optical detector array and the transmission spectrum of the one or more optical filters.

In various embodiments, processing electronics can be configured to process the IR radiation detected by the optical detection unit. The processing electronics can be configured to generate an image representative of the detected IR radiation and to render the image for display on a display device.

In some embodiments, a second non-target species can be associated with a second absorption spectrum. A convolution of the spectral response curve with the second absorption spectrum can be less than the convolution of the spectral response curve with the absorption spectrum of the target species. In various embodiments, the system comprises a single optical channel for imaging.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In the drawings like numbers are used to represent the same or similar elements wherever possible. The depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The features recited in claims appended to this disclosure are intended to be assessed in light of the disclosure as a whole.

At least some elements of a device of the invention can be controlled—and at least some steps of a method of the invention can be effectuated, in operation—with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While examples of embodiments of the system and method of the invention have been discussed in reference to the gas-cloud detection, monitoring, and quantification of gases such as methane, other embodiments can be readily adapted for other chemical detection applications. For example, detection of liquid and solid chemical spills, biological weapons, tracking targets based on their chemical composition, identification of satellites and space debris, ophthalmological imaging, microscopy and cellular imaging, endoscopy, mold detection, fire and flame detection, and pesticide detection are within the scope of the invention.

As used herein, a phrase referring to "at least one of" a list of items refers to any combination of those items, including single members. As an example, "at least one of: a, b, or c" is intended to cover: a, b, c, a-b, a-c, b-c, and a-b-c.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. An infrared (IR) imaging system for detecting methane, the imaging system comprising:
an optical detection unit comprising:
an optical detector array, wherein sensitivity of the optical detector array in a spectral region between 4-6 microns is less than the sensitivity of the optical detector array in a first infrared spectral region between 3-4 microns and a second infrared spectral region between 6-8 microns; and
one or more optical filters configured to selectively pass light in a spectral range,
wherein a convolution of responsivity of the optical detector array and a transmission spectrum of the one or more optical filters has a first peak in the first infrared spectral region between 3-4 microns corresponding to a first absorption peak of methane and a second peak in the second infrared spectral region between 6-8 microns corresponding to a second absorption peak of methane, wherein said optical detection unit does not include a cooler configured to cool the optical detector array to a temperature below 200 Kelvin.

2. The imaging system of claim 1, configured to be portable.

3. The imaging system of claim 1, configured to be handheld.

4. The imaging system of claim 1, configured to be battery-operated.

5. The imaging system of claim 1, further comprising a display, the imaging system configured to render a concentration of methane in real-time or near real-time on the display.

6. The imaging system of claim 5, wherein the imaging system is configured to render the concentration of methane at various spatial locations in real-time or near real-time on the display.

7. The infrared imaging system of claim 1, wherein said imaging system comprises a single channel infrared imaging system, said optical detection unit providing a single infrared channel.

8. An infrared (IR) imaging system configured to detect and identify a target species associated with an absorption spectrum, the IR imaging system comprising:
a single channel optical detection unit comprising an optical detector array configured to detect IR radiation, the optical detection unit characterized by a spectral response curve defining a responsivity of the optical detection unit to IR radiation across a range of wavelengths,
wherein a convolution of the spectral response curve with the absorption spectrum of the target species defines a first peak at a first wavelength and a second peak at a second wavelength different from the first wavelength, said second wavelength being at least 2 microns from said first wavelength, wherein said single channel optical detection unit does not include a cooler configured to cool the optical detector array to a temperature below 200 Kelvin.

9. The IR imaging system of claim 8, wherein the convolution comprises an attenuated region between the first peak and the second peak, wherein the first peak is at least five times as large as the attenuated region.

10. The IR imaging system of claim 8, wherein the first wavelength is in a range of 3 microns to 4 microns.

11. The IR imaging system of claim 8, wherein the second wavelength is in a range of 6 microns to 8 microns.

12. The IR imaging system of claim 8, wherein the target species comprises methane gas.

13. The IR imaging system of claim 8, wherein the optical detection unit further comprises one or more optical filters configured to selectively pass light in the range of wavelengths.

14. The IR imaging system of claim 13, wherein the spectral response curve of the optical detection unit is characterized by a convolution of responsivity of the optical detector array and a transmission spectrum of the one or more optical filters.

15. The IR imaging system of claim 8, further comprising processing electronics configured to process the IR radiation detected by the optical detection unit, the processing electronics configured to generate an image representative of the detected IR radiation and to render the image for display on a display device.

16. The IR imaging system of claim 8, wherein a second non-target species is associated with a second absorption spectrum, wherein a convolution of the spectral response curve with the second absorption spectrum is less than the convolution of the spectral response curve with the absorption spectrum of the target species.

17. The system of claim 8, wherein the target species comprises methane.

18. A spectral imaging system configured to image a target species, said system comprising:
an optical detecting unit comprising an optical detector array configured to capture an image of a scene, the optical detecting unit configured to have increased sensitivity to one or more wavelengths less than 8.3 microns,
wherein the optical detecting unit does not include a cooler configured to cool the optical detector array to a temperature below 200 Kelvin, and
wherein said spectral imaging system comprises a single channel infrared imaging system, said optical detecting unit providing a single infrared channel, and said target species is methane.

19. The imaging system of claim 18, wherein the optical detecting unit is configured to have increased sensitivity to one or more wavelengths between 3 and 4 microns.

20. The imaging system of claim 18, wherein the optical detecting unit comprises a transmissive window configured to transmit a plurality of wavelengths between 2 microns and 8 microns.

* * * * *